United States Patent
Masuda et al.

(10) Patent No.: US 9,801,579 B2
(45) Date of Patent: Oct. 31, 2017

(54) AROUSAL-LEVEL DETERMINING APPARATUS AND AROUSAL-LEVEL DETERMINING METHOD

(71) Applicant: FUJITSU LIMITED, Kawasaki-shi, Kanagawa (JP)

(72) Inventors: Yuta Masuda, Kawasaki (JP); Satoshi Sano, Kawasaki (JP); Junichi Odagiri, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 41 days.

(21) Appl. No.: 14/479,488

(22) Filed: Sep. 8, 2014

(65) Prior Publication Data

US 2014/0378857 A1    Dec. 25, 2014

Related U.S. Application Data

(63) Continuation of application No. PCT/JP2012/057073, filed on Mar. 19, 2012.

(51) Int. Cl.
*A61B 5/18* (2006.01)
*A61B 5/0402* (2006.01)
(Continued)

(52) U.S. Cl.
CPC .............. *A61B 5/18* (2013.01); *A61B 5/0245* (2013.01); *A61B 5/02405* (2013.01);
(Continued)

(58) Field of Classification Search
CPC ..... A61B 5/18; A61B 5/02405; A61B 5/0245; A61B 5/0402; A61B 5/681;
(Continued)

(56) References Cited

U.S. PATENT DOCUMENTS 6,126,595 A * 10/2000 Amano ................... A61B 5/02
                                                    600/300
7,970,459 B2    6/2011 Karasudani
(Continued)

FOREIGN PATENT DOCUMENTS

EP    2087841 A1    12/2009
JP    2000-300528 A    10/2000
(Continued)

OTHER PUBLICATIONS

Extended European Search Report dated Nov. 18, 2014 for corresponding European Patent Application 12872173.5, 7 pages.
(Continued)

*Primary Examiner* — Carl H Layno
*Assistant Examiner* — Erin M Piateski
(74) *Attorney, Agent, or Firm* — Fujitsu Patent Center

(57) ABSTRACT

An arousal-level determining apparatus includes a generating unit, a calculating unit, an identifying unit, and a determining unit. The generating unit generates heartbeat-interval variation data, which indicates changes in heartbeat interval, on the basis of heartbeat signals indicating subject's heartbeats. The calculating unit applies a band-pass filter, which allows passage of a certain range of frequencies, to each frequency band in the heartbeat-interval variation data while changing the frequency band, and calculates spectral density with respect to each frequency band applied with the band-pass filter. The identifying unit identifies a feature point corresponding to a spectral density peak in the calculated spectral densities in the frequency bands. The determining unit determines subject's arousal level on the basis of the identified feature point.

8 Claims, 18 Drawing Sheets

(51) Int. Cl.
*A61B 5/00* (2006.01)
*A61B 5/024* (2006.01)
*A61B 5/0245* (2006.01)
*A61B 5/04* (2006.01)

(52) U.S. Cl.
CPC ............ *A61B 5/0402* (2013.01); *A61B 5/681* (2013.01); *A61B 5/04015* (2013.01); *A61B 5/04018* (2013.01); *A61B 5/6893* (2013.01); *A61B 5/6898* (2013.01); *A61B 5/7257* (2013.01); *A61B 2503/22* (2013.01)

(58) Field of Classification Search
CPC ............ A61B 5/04015; A61B 5/04018; A61B 5/6893; A61B 5/6898; A61B 5/7257; A61B 2503/22
USPC .......................................................... 600/519
See application file for complete search history.

(56) References Cited

U.S. PATENT DOCUMENTS

| | | | |
|---|---|---|---|
| 2002/0128564 A1* | 9/2002 | Carlson | A61B 5/02405 600/509 |
| 2003/0163033 A1 | 8/2003 | Dekker | |
| 2003/0163034 A1 | 8/2003 | Dekker | |
| 2003/0163050 A1 | 8/2003 | Dekker | |
| 2003/0163054 A1 | 8/2003 | Dekker | |
| 2004/0260186 A1 | 12/2004 | Dekker | |
| 2006/0036183 A1* | 2/2006 | Sackner | A61B 5/0205 600/481 |
| 2009/0082642 A1* | 3/2009 | Fine | A61B 5/0059 600/300 |
| 2009/0275847 A1* | 11/2009 | Karasudani | A61B 5/024 600/509 |
| 2011/0224565 A1* | 9/2011 | Ong | G06F 19/345 600/509 |

FOREIGN PATENT DOCUMENTS

| | | |
|---|---|---|
| JP | 2005-535359 A | 11/2005 |
| JP | 2010-155072 A | 7/2010 |
| WO | 2007144880 A2 | 12/2007 |
| WO | 2008/065724 A1 | 6/2008 |
| WO | 2010082200 A1 | 7/2010 |
| WO | 2010/140241 A1 | 12/2010 |
| WO | 2010/140273 A1 | 12/2010 |

OTHER PUBLICATIONS

International Search Report, mailed in connection with PCT/JP2012/057073 and mailed Jun. 5, 2012.

* cited by examiner

AROUSAL-LEVEL DETERMINING APPARATUS AND AROUSAL-LEVEL DETERMINING METHOD

CROSS-REFERENCE TO RELATED APPLICATION

This application is a continuation application of International Application PCT/JP2012/057073, filed on Mar. 19, 2012, and designating the U.S., the entire contents of which are incorporated herein by reference.

FIELD

The present invention relates to an arousal-level determining apparatus, an arousal-level determining program, and an arousal-level determining method.

BACKGROUND

Conventionally, there are technologies for determining subject's arousal level with no burden on a subject by using subject's biological information. For example, there is a conventional technology to track changes in a feature point at which spectral density calculated from subject's heartbeat signals by frequency analysis reaches its local maximum, thereby determining subject's arousal level. For example, by applying this conventional technology to a vehicle, driver's arousal level can be determined, and it is possible to inform the driver of a risk.

To determine subject's arousal level by using this conventional technology, it is necessary to acquire a feature point stably.

Patent Literature 1: Japanese Laid-open Patent Publication No. 2010-155072

Patent Literature 2: International Publication Pamphlet No. WO 2008/065724

However, there is a problem that if a feature point calculated from heartbeat signals by frequency analysis is indistinct, it may fail to determine subject's arousal level.

SUMMARY

According to an aspect of an embodiment, an arousal-level determining apparatus includes a generating unit that generates heartbeat-interval variation data, which indicates changes in heartbeat interval, on the basis of heartbeat signals indicating subject's heartbeats; a calculating unit that applies a band-pass filter, which allows passage of a certain range of frequencies, to each frequency band in the heartbeat-interval variation data while changing the frequency band, and calculates spectral density with respect to each frequency band applied with the band-pass filter; an identifying unit that identifies a feature point corresponding to a spectral density peak in the spectral densities in the frequency bands calculated by the calculating unit; and a determining unit that determines subject's arousal level on the basis of the feature point identified by the identifying unit.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Embodiments of an arousal-level determining apparatus, arousal-level determining program, and arousal-level determining method discussed in the present application will be explained in detail below on the basis of accompanying drawings. Incidentally, the embodiments do not limit the technology discussed herein. Then, the embodiments can be arbitrarily combined within the scope which does not contradict processing contents.

First Embodiment

[Configuration of Arousal-Level Determining Apparatus 100]

Figure 1:
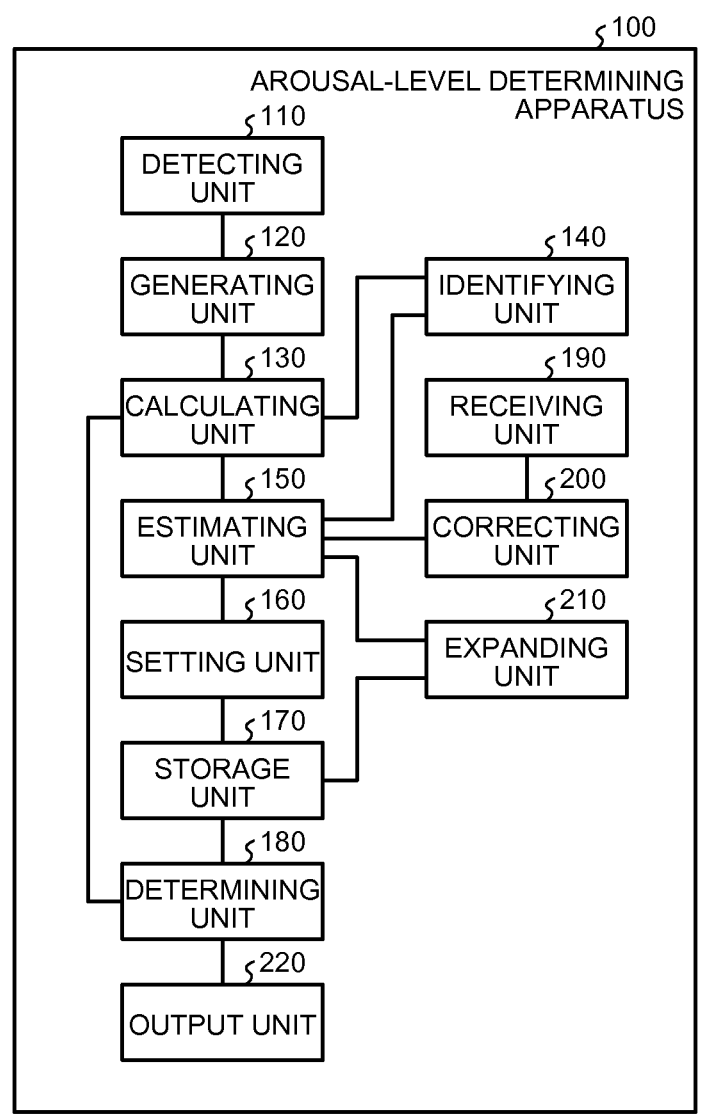
FIG. 1 is a diagram illustrating a configuration of an arousal-level determining apparatus according to a present first embodiment.

An example of a configuration of an arousal-level determining apparatus according to a present first embodiment is explained. FIG. 1 is a diagram illustrating the configuration of the arousal-level determining apparatus according to the present first embodiment. An arousal-level determining apparatus 100 is an apparatus for determining subject's arousal level, and is, for example, a computer. As illustrated in FIG. 1, this arousal-level determining apparatus 100 includes a detecting unit 110, a generating unit 120, a calculating unit 130, an identifying unit 140, an estimating unit 150, and a setting unit 160. Furthermore, the arousal-level determining apparatus 100 further includes a storage unit 170, a determining unit 180, a receiving unit 190, a correcting unit 200, an expanding unit 210, and an output unit 220.

The detecting unit 110 detects subject's heartbeat signals. For example, the detecting unit 110 applies voltage to electrodes in contact with a subject, and acquires subject's heartbeat signals from a difference in potential between the electrodes. Incidentally, the subject corresponds to, for example, a driver who drives a vehicle. Furthermore, the electrodes used by the detecting unit 110 correspond to, for example, electrodes embedded in the steering wheel of the vehicle. Moreover, for example, when the arousal-level determining apparatus 100 is constituted as wristwatch-type small equipment, the electrodes used by the detecting unit 110 correspond to electrodes embedded in the wristwatch-type small equipment.

Figure 2:
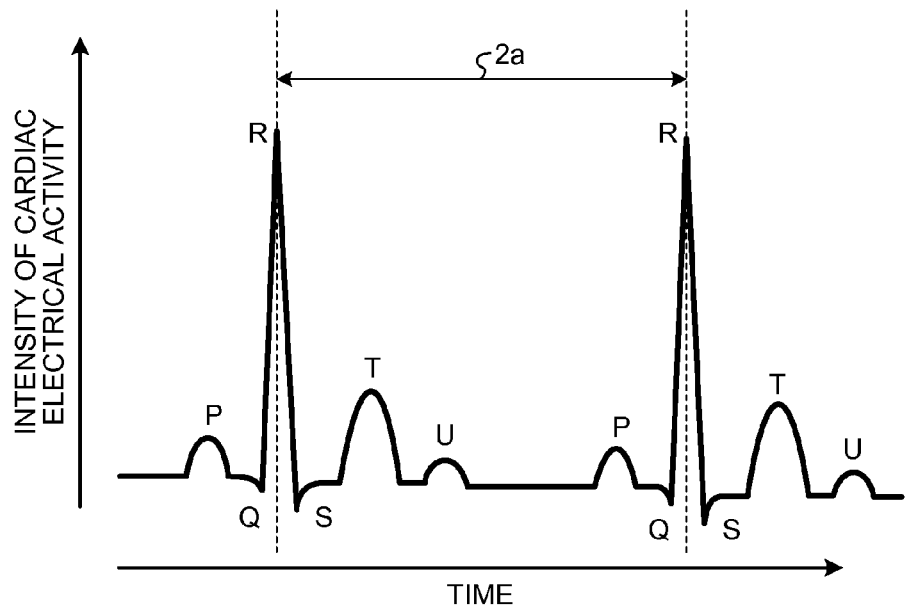
FIG. 2 is a diagram illustrating an example of heartbeat signals detected by a detecting unit.

FIG. 2 is a diagram illustrating an example of the heartbeat signals detected by the detecting unit. The horizontal axis in FIG. 2 indicates passage of time, and the vertical axis indicates intensity of cardiac electrical activity. In general, a healthy person's cardiac heartbeat signal has four waveforms as illustrated in FIG. 2, and the four waveforms are called a P wave, a QRS complex, a T wave, and a U wave in chronological order. In particular, the QRS complex is detected as an acute-angled peak, and includes a Q wave which is the starting point of the peak, an R wave which is the apex of the peak, and an S wave which is the end point of the peak. One set of the waveforms from the P wave to the U wave corresponds to one heartbeat. An R-R interval 2a calculated as an interval between R waves corresponds to a heartbeat interval indicating a time interval between heartbeats. The detecting unit 110 outputs data of the detected heartbeat signals as heartbeat signal data to the generating unit 120.

Figure 3:
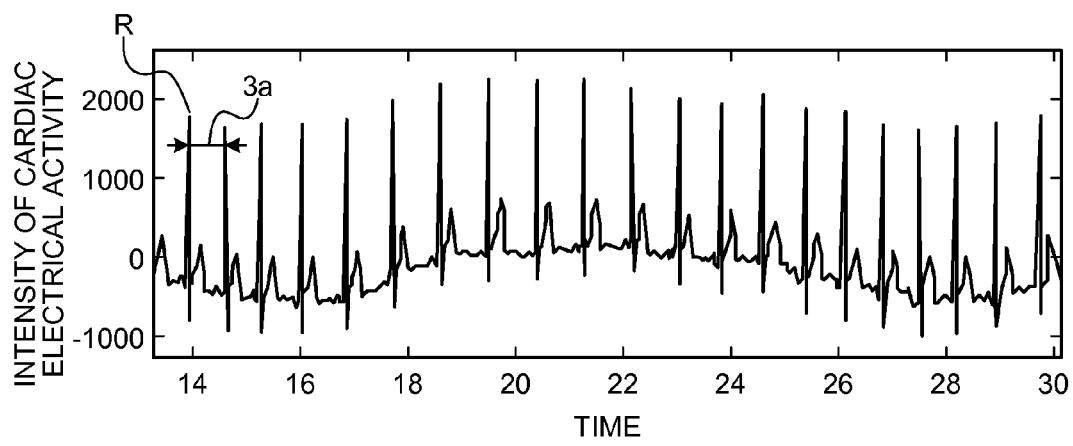
FIG. 3 is a diagram for explaining a heartbeat-interval calculating process performed by a generating unit.

The generating unit 120 generates heartbeat-interval variation data, which indicates changes in heartbeat interval, on the basis of subject's heartbeat signal data. A process performed by the generating unit 120 is explained in detail below. The generating unit 120 calculates heartbeat intervals from the heartbeat signal data input by the detecting unit 110. FIG. 3 is a diagram for explaining a heartbeat-interval calculating process performed by the generating unit 120. The horizontal axis in FIG. 3 indicates passage of time, and the vertical axis indicates intensity of cardiac electrical activity.

As illustrated in FIG. 3, the generating unit 120 detects an amplitude peak at which the amplitude of a heartbeat signal exceeds a threshold value as an R wave. Then, each time the generating unit 120 detects an R wave, the generating unit 120 calculates a heartbeat interval 3a from the appearance time of each detected R wave. Incidentally, an amplitude-peak detection method is not limited to the above-described method. For example, the generating unit 120 can use a method using a zero crossing point at which a differential coefficient of a heartbeat signal changes from positive to negative and a method for detecting an amplitude peak by performing pattern matching on each amplitude waveform, etc.

Figure 4:
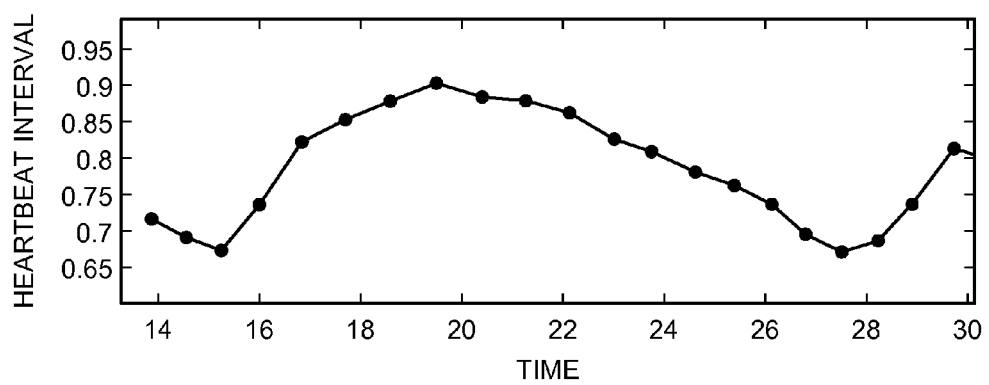
FIG. 4 is a diagram illustrating an example of heartbeat-interval variation data generated by the generating unit.

The generating unit 120 generates heartbeat-interval variation data, which indicates changes in heartbeat interval with the passage of time, on the basis of the calculated heartbeat intervals. FIG. 4 is a diagram illustrating an example of the heartbeat-interval variation data generated by the generating unit. The horizontal axis in FIG. 4 indicates passage of time, and the vertical axis indicates heartbeat interval. As illustrated in FIG. 4, for example, the generating unit 120 generates heartbeat-interval variation data associated with the calculated heartbeat intervals and the detection time of each R wave.

The calculating unit 130 calculates a feature amount which indicates subject's arousal level. For example, the calculating unit 130 performs frequency analysis on the heartbeat-interval variation data, thereby calculating spectral density with respect to each frequency. For example, the calculating unit 130 uses an auto-regressive (AR) model to calculate spectral density. As disclosed in Non-patent Literature (SATO Shunsuke, KIKKAWA Sho, and KIRYU Tohru, *Basics of Biosignal Processing*, CORONA PUBLISHING CO., LTD.) and the like, an AR model is a model that expresses a state at a certain point of time in the linear sum of previous time-series data. The AR model has a characteristic of enabling a distinct local maximum point even though the number of data is small as compared with Fourier transform.

For example, a p-th order AR model for a time series x(s) is expressed by the following equation (1) using an AR coefficient a(m), which is a weight put on a previous value, and an error term e(s). Incidentally, ideally, e(s) is a white noise.

$$x(s) = \sum_{m=1}^{P} a(m)x(s-m) + e(s) \quad (1)$$

Then, the following (2) is a k-th order AR coefficient, where p is identification order, $f_s$ is a sampling frequency, and $\epsilon_p$ is an identification error.

$$\hat{a}_p(k) \quad (2)$$

In this case, spectral density $P_{AR}(f)$ is expressed by the following equation (3).

$$P_{AR}(f) = \frac{1}{f_s} \frac{\varepsilon_P}{\left|1 + \sum_{k=1}^{P} \hat{a}_P(k)e^{-2\pi jkf/f_k}\right|^2} \quad (3)$$

The calculating unit 130 calculates spectral density on the basis of the equation (3) and the heartbeat-interval variation data. Incidentally, a method for calculating spectral density is not limited to the above-described method. For example, the calculating unit 130 can calculate spectral density by using Fourier transform.

Each time the calculating unit 130 calculates spectral density, the calculating unit 130 generates spectral density data which indicates spectral density at each frequency. FIG.

Figure 5:
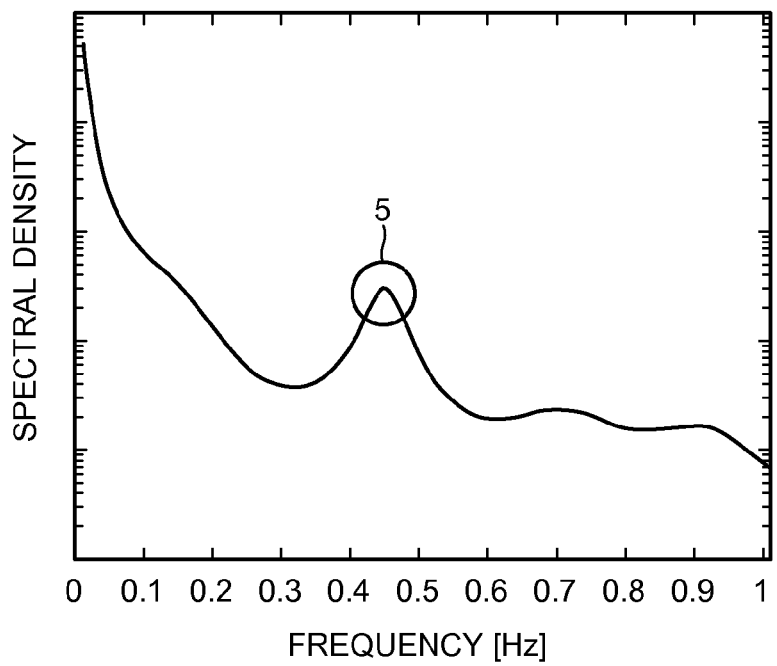
FIG. 5 is a diagram illustrating an example of spectral density data generated by a calculating unit.

5 is a diagram illustrating an example of the spectral density data generated by the calculating unit. The horizontal axis in FIG. 5 indicates frequency, and the vertical axis indicates spectral density.

Figure 6:
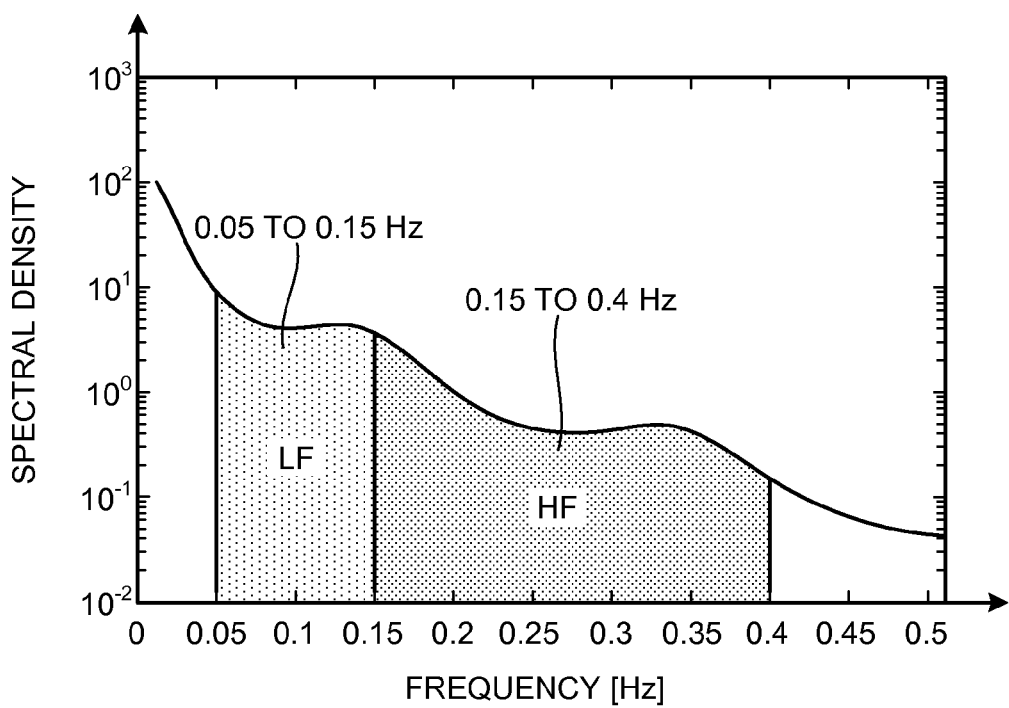
FIG. 6 is a diagram for explaining characteristics of frequency bands.

Incidentally, the spectral density has the following characteristics in frequency bands. FIG. 6 is a diagram for explaining the characteristics of the frequency bands. The horizontal axis in FIG. 6 indicates frequency, and the vertical axis indicates spectral density. A spectral density component appearing, for example, in an area of 0.05 to around 0.15 Hz is a low-frequency (LF) component that reflects a state of sympathetic nerve activity. Furthermore, a spectral density component appearing, for example, in an area of 0.15 to around 0.4 Hz is a high-frequency (HF) component that reflects a state of parasympathetic nerve activity.

The calculating unit 130 acquires a local maximum point at which spectral density of the spectral density data reaches its local maximum. For example, the calculating unit 130 calculates a frequency f which satisfies the following equation (4) as a frequency at the local maximum point, and substitutes the frequency at the local maximum point into the equation (3), thereby calculating spectral density at the local maximum point.

$$\frac{dP_{AR}(f)}{df} = 0 \qquad (4)$$

Figure 7:
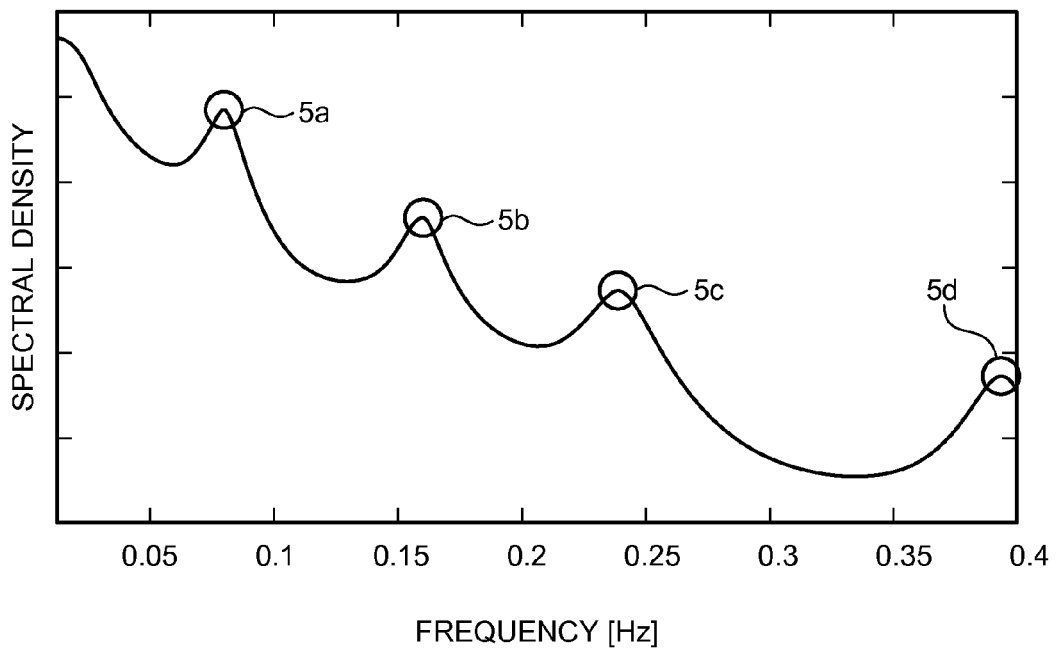
FIG. 7 is a diagram illustrating an example where multiple local maximum points exist.

The calculating unit 130 acquires a local maximum point included in the HF component. In the example illustrated in FIG. 5, the calculating unit 130 acquires a local maximum point 5. Incidentally, in the following description, a frequency at a local maximum point is referred to as a "local maximum frequency", and spectral density at the local maximum point is referred to as "local maximum spectral density". Incidentally, when multiple local maximum points exist, a local maximum point is selected as follows. FIG. 7 is a diagram illustrating an example where multiple local maximum points exist. The horizontal axis in FIG. 7 indicates frequency, and the vertical axis indicates spectral density. In the example illustrated in FIG. 7, four local maximum points 5a, 5b, 5c, and 5d exist. The calculating unit 130 acquires the four local maximum points 5a, 5b, 5c, and 5d.

The calculating unit 130 selects one local maximum point included in the HF component from among the acquired four local maximum points 5a, 5b, 5c, and 5d. When multiple local maximum points are included in the HF component as illustrated in FIG. 7, the calculating unit 130 selects the local maximum point 5b having the lowest frequency among those included in the HF component. This is because a local maximum point on the low-frequency side out of local maximum points included in the HF component reflects a breathing state. On the other hand, a local maximum point on the high-frequency side also reflects a breathing state but is affected by something other than breathing, for example, even by body movement. In general, when a subject is in a non-arousal state in which sleepiness is strong, the subject breathes slowly; therefore, it is considered that by selecting a local maximum point which reflects a breathing state more strongly, subject's sleepiness can be determined more accurately.

Figure 8:
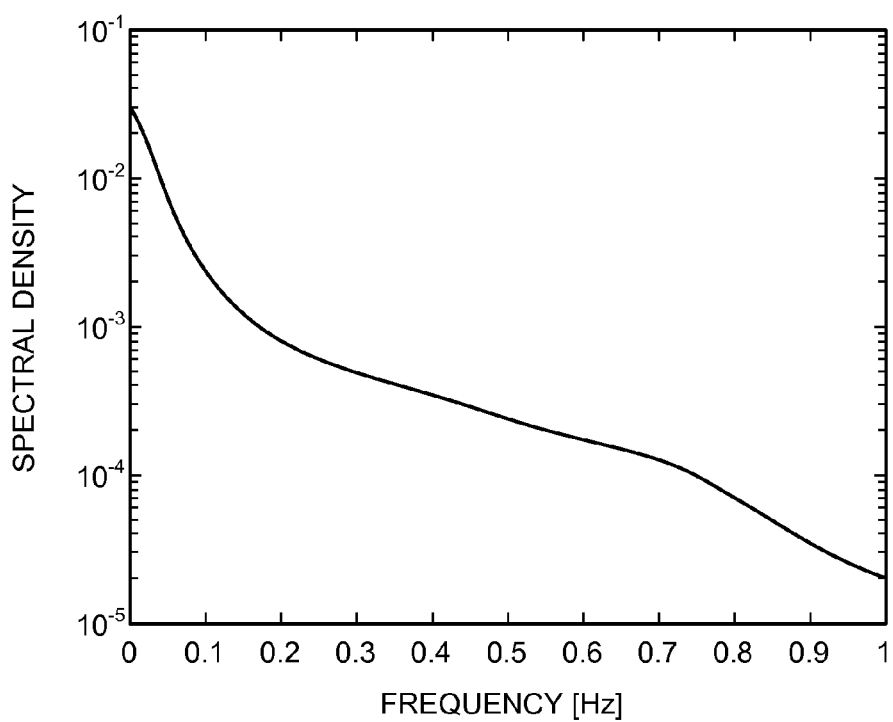
FIG. 8 is a diagram illustrating an example of spectral density data with an indistinct local maximum point.

Incidentally, changes in heartbeat interval indicated by the heartbeat-interval variation data include a sympathetic nerve activity component and a noise component due to body movement, etc. besides a parasympathetic component. For example, in a state where sympathetic nerve activity has been activated by a stress or a struggle against sleepiness thereby the LF component has increased or a state where the noise component has increased by body movement, etc., a local maximum point becomes indistinct due to the influence of the component, and It is difficult to obtain a sleepiness index value. FIG. 8 is a diagram illustrating an example of spectral density data with an indistinct local maximum point. The horizontal axis in FIG. 8 indicates frequency, and the vertical axis indicates spectral density. In the example illustrated in FIG. 8, the spectral density changes gently, and no local maximum point exists. Such a state where the spectral density changes gently does not appear when a subject is in any particular state, and a causal relationship with subject's state is not found. Then, in such a state where the spectral density changes gently, no local maximum point exists; therefore, it is not possible to determine the state of subject's sleepiness.

Therefore, when no local maximum point exists in the HF component of the calculated spectral density, the calculating unit 130 calculates spectral density through the application of a band-pass filter. For example, the calculating unit 130 applies the band-pass filter, which allows passage of a certain range of frequencies, to each frequency band in the heartbeat-interval variation data while changing the frequency band, and calculates spectral density in each frequency band applied with the band-pass filter.

When the band-pass filter is appropriately applied to a spectrum of which the peak is indistinct, spectrum power tends to increase; however, when the spectrum is out of the range, power tends to decrease. Therefore, the calculating unit 130 calculates spectral density through the application of the band-pass filter. This makes it easier to detect the spectral density peak. The passband width of this band-pass filter is preferably a range of frequencies in which the feature point to be described later shifts with a change in arousal level. With changes in arousal level, a feature point to be described later shifts by about 0.1 to 0.2 Hz. In the present embodiment, the passband width of the band-pass filter shall be 0.2 Hz; however, it is not limited to this. The passband width of the band-pass filter can be set to any value by a person who uses the arousal-level determining apparatus 100.

Figure 9:
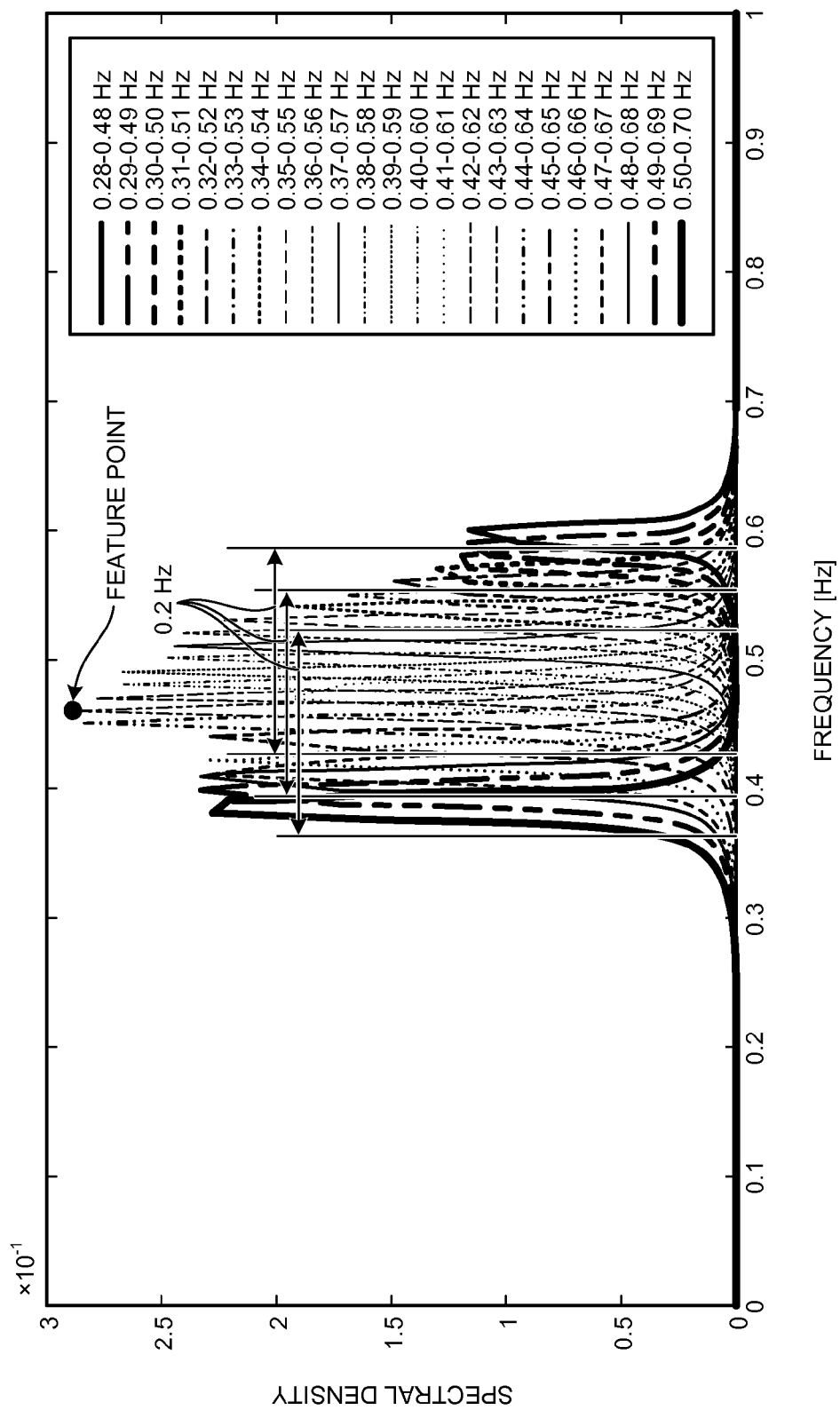
FIG. 9 is a diagram for explaining a process of calculating spectral density through the application of a band-pass filter.

Furthermore, the calculating unit 130 calculates spectral density with respect to each frequency band while changing the frequency band applied with the band-pass filter to be partially overlapped with a previous frequency band applied. For example, the calculating unit 130 calculates spectral density by applying the band-pass filter to each frequency band in the heartbeat-interval variation data while changing the band to be applied within a frequency range of the HF component by an amount smaller than the passband width of the band-pass filter. In the present embodiment, the change amount shall be 0.01 Hz smaller than 0.2 Hz, the passband width of the band-pass filter; however, it is not limited to this. The change amount of a frequency band applied with the band-pass filter can be set to any value by a person who uses the arousal-level determining apparatus 100. While sliding a frequency range within a frequency range of the HF component by 0.01 Hz, the calculating unit 130 applies the band-pass filter to the frequency range, thereby calculating spectral density. FIG. 9 is a diagram for explaining a process of calculating spectral density through the application of the band-pass filter. The horizontal axis in FIG. 9 indicates frequency, and the vertical axis indicates spectral density. The example illustrated in FIG. 9 indicates results of spectral density calculated by applying the band-pass filter with the passband width of 0.2 Hz to a frequency band while changing the applied band within a frequency range of 0.28 to 0.5 Hz by 0.01 Hz.

The identifying unit 140 identifies a feature point. For example, the identifying unit 140 identifies a feature point corresponding to a spectral density peak in respective spectral densities in the frequency bands calculated by the calculating unit 130. In the example illustrated in FIG. 9, the identifying unit 140 compares the calculated spectral densities in the frequency bands, and identifies a feature point corresponding to a spectral density peak in the spectral densities in the frequency range of the HF component. Incidentally, a method for identifying the feature point is not limited to the above-described method. For example, the identifying unit 140 can use a method to identify the feature point corresponding to a spectral density peak by interpolating respective local maximum spectral density values in the frequency bands calculated by the calculating unit 130 by interpolation, such as spline interpolation.

Figure 10:
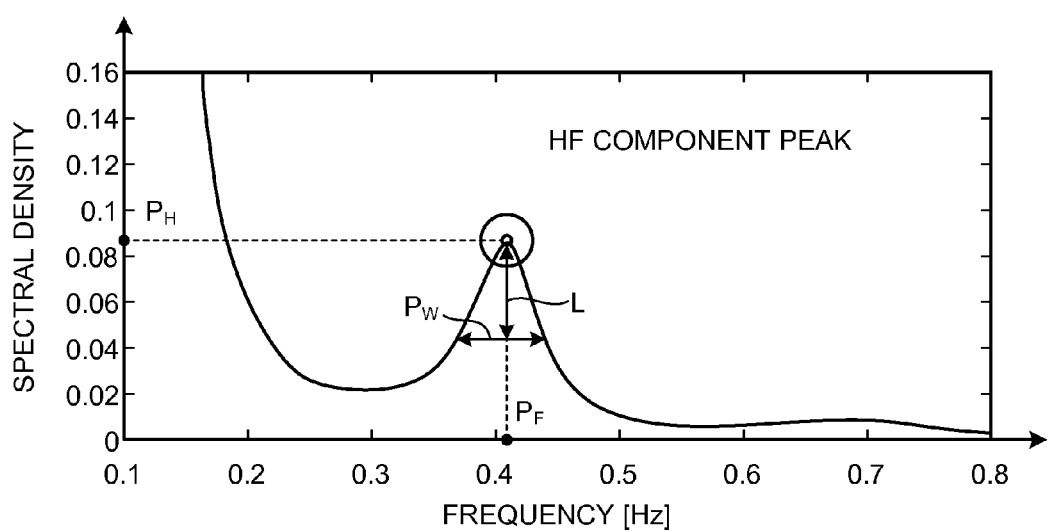
FIG. 10 is a diagram illustrating an example of a local maximum frequency, local maximum spectral density, and the width of a spectrum waveform.

When the calculating unit 130 was able to acquire a local maximum point included in the HF component, the calculating unit 130 calculates a local maximum frequency and local maximum spectral density at the acquired local maximum point as a feature amount. Furthermore, the calculating unit 130 acquires a value of width Pw of a spectrum waveform at a certain height L from the local maximum point. This height L can be a fixed value, or can be the predetermined ratio of peak height such as half width. Furthermore, the height L can be set to any value by a person who uses the arousal-level determining apparatus 100. On the other hand, when the calculating unit 130 was not able to acquire a local maximum point included in the HF component, the calculating unit 130 calculates a local maximum frequency and local maximum spectral density at the feature point corresponding to a spectral density peak in the spectral densities calculated with respect to each frequency band through the application of the band-pass filter as a feature amount. Furthermore, the calculating unit 130 interpolates respective local maximum spectral density values calculated with respect to each frequency band by interpolation, such as spline interpolation, and acquires a value of width Pw of a spectrum waveform at a certain height L from the feature point corresponding to a spectral density peak. FIG. 10 is a diagram illustrating an example of a local maximum frequency, local maximum spectral density, and the width of a spectrum waveform. The horizontal axis in FIG. 10 indicates frequency, and the vertical axis indicates spectral density. In the example illustrated in FIG. 10, the local maximum frequency is denoted by $P_F$, the local maximum spectral density is denoted by $P_H$, and the width of the spectrum waveform at the certain height L from the local maximum point is denoted by $P_W$.

Figure 11:
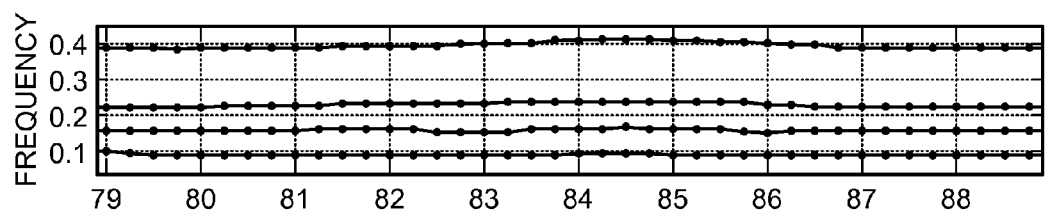
FIG. 11 is a diagram indicating a local maximum frequency in a time series.
Figure 12:
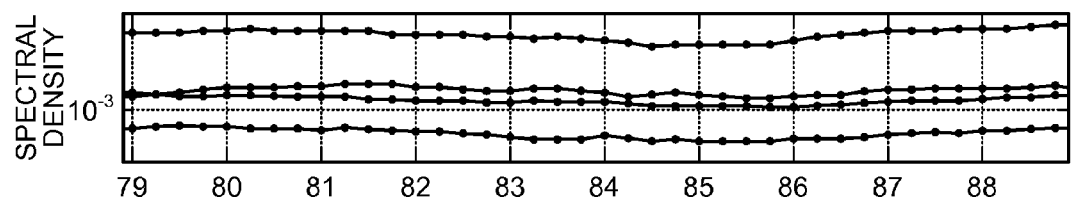
FIG. 12 is a diagram indicating local maximum spectral density in a time series.

FIG. 11 is a diagram indicating a local maximum frequency in a time series. The horizontal axis in FIG. 11 indicates passage of time, and the vertical axis indicates frequency. FIG. 12 is a diagram indicating local maximum spectral density in a time series. The horizontal axis in FIG. 12 indicates passage of time, and the vertical axis indicates spectral density. When the calculating unit 130 calculates spectral density data at intervals of 10 seconds, the interval between points in a time-series direction illustrated in FIGS. 11 and 12 is a 10-second interval. As illustrated in FIGS. 11 and 12, the calculating unit 130 calculates a local maximum frequency and local maximum spectral density at regular time intervals.

Return to the explanation of FIG. 1. The estimating unit 150 estimates a feature amount during non-arousal from the feature amount calculated by the calculating unit 130 on the basis of a correlation between a feature amount during arousal and a feature amount during non-arousal. For example, using the fact that a local maximum frequency and local maximum spectral density are correlated between during arousal and during non-arousal, the estimating unit 150 estimates a value during non-arousal from values for a few minutes from the start of driving. Using values for a few minutes from the start of driving here is because a driver is considered to be awake in this period of time, so a feature amount during arousal can be acquired certainly.

Figure 13:
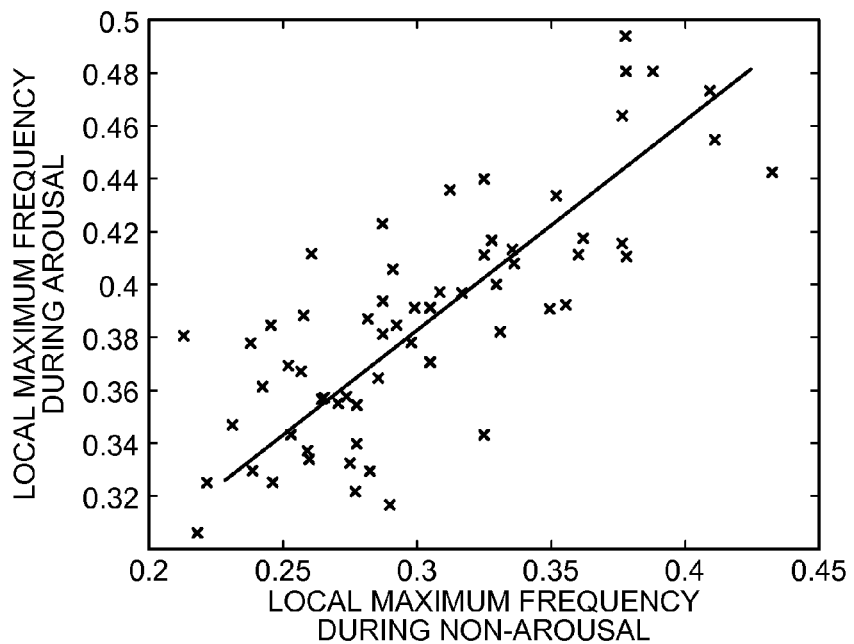
FIG. 13 is a diagram illustrating a correlation between a local maximum frequency during arousal and a local maximum frequency during non-arousal.
Figure 14:
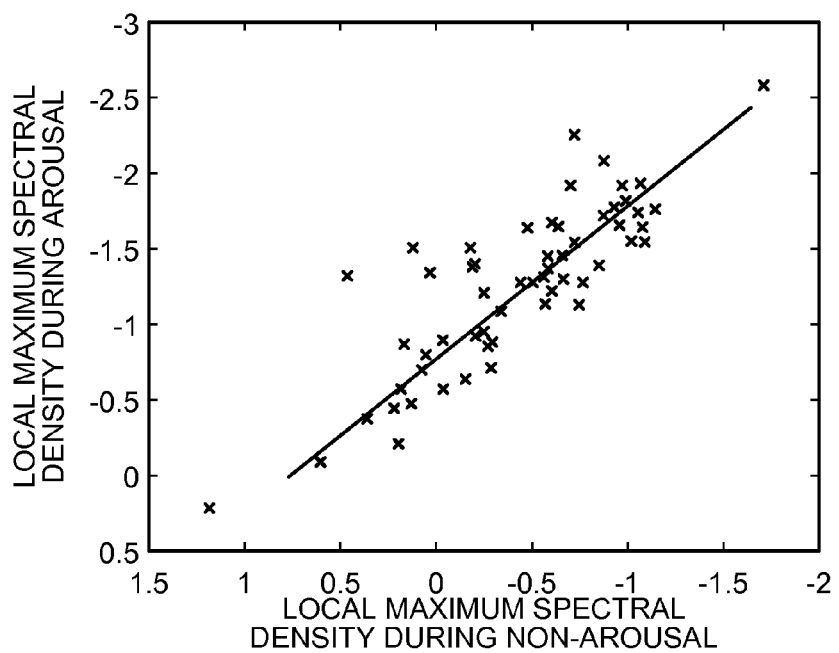
FIG. 14 is a diagram illustrating a correlation between local maximum spectral density during arousal and local maximum spectral density during non-arousal.

Here, the correlation used by the estimating unit 150 is explained. FIG. 13 is a diagram illustrating a correlation between a local maximum frequency during arousal and a local maximum frequency during non-arousal. The horizontal axis in FIG. 13 indicates local maximum frequency during non-arousal, and the vertical axis indicates local maximum frequency during arousal. FIG. 14 is a diagram illustrating a correlation between local maximum spectral density during arousal and local maximum spectral density during non-arousal. The horizontal axis in FIG. 14 indicates local maximum spectral density during non-arousal, and the vertical axis indicates local maximum spectral density during arousal.

FIGS. 13 and 14 are an example of experimental results of an experiment for acquiring subjects' heartbeat signals with use of a driving simulator. As illustrated in FIGS. 13 and 14, when respective values during subjects' arousal and values during subjects' non-arousal were plotted, a regression line is obtained. These experimental results indicate that a local maximum frequency and local maximum spectral density are correlated between during arousal and during non-arousal. Incidentally, in the examples illustrated in FIGS. 13 and 14, a correlation coefficient of a local maximum frequency is 0.78, and a correlation coefficient of local maximum spectral density is 0.85.

For example, the estimating unit 150 acquires a local maximum frequency and local maximum spectral density from the calculating unit 130. When subject's scale has not been set, the estimating unit 150 sets the acquired local maximum frequency and local maximum spectral density as a reference point. The estimating unit 150 substitutes the local maximum frequency and local maximum spectral density set as the reference point into linear regression equations illustrated in FIGS. 13 and 14, thereby calculating a local maximum frequency and local maximum spectral density during non-arousal. Then, the estimating unit 150 sets the calculated local maximum frequency and local maximum spectral density during non-arousal as an estimated point, and outputs the reference point and the estimated point to the setting unit 160. On the other hand, when subject's scale has been set, the estimating unit 150 outputs the acquired local maximum frequency and local maximum spectral density to the expanding unit 210.

Furthermore, when the reference point has been corrected by the correcting unit 200 to be described later, the estimating unit 150 estimates an estimated point by using the corrected reference point. Then, the estimating unit 150 outputs the reference point and the estimated point to the setting unit 160.

The setting unit 160 sets a range from the feature amount calculated by the calculating unit 130 to the feature amount estimated by the estimating unit 150 as an index of arousal level. For example, the setting unit 160 sets respective variable ranges of frequency and spectral density between the reference point and the estimated point as a scale serving as an index of arousal level.

Figure 15:
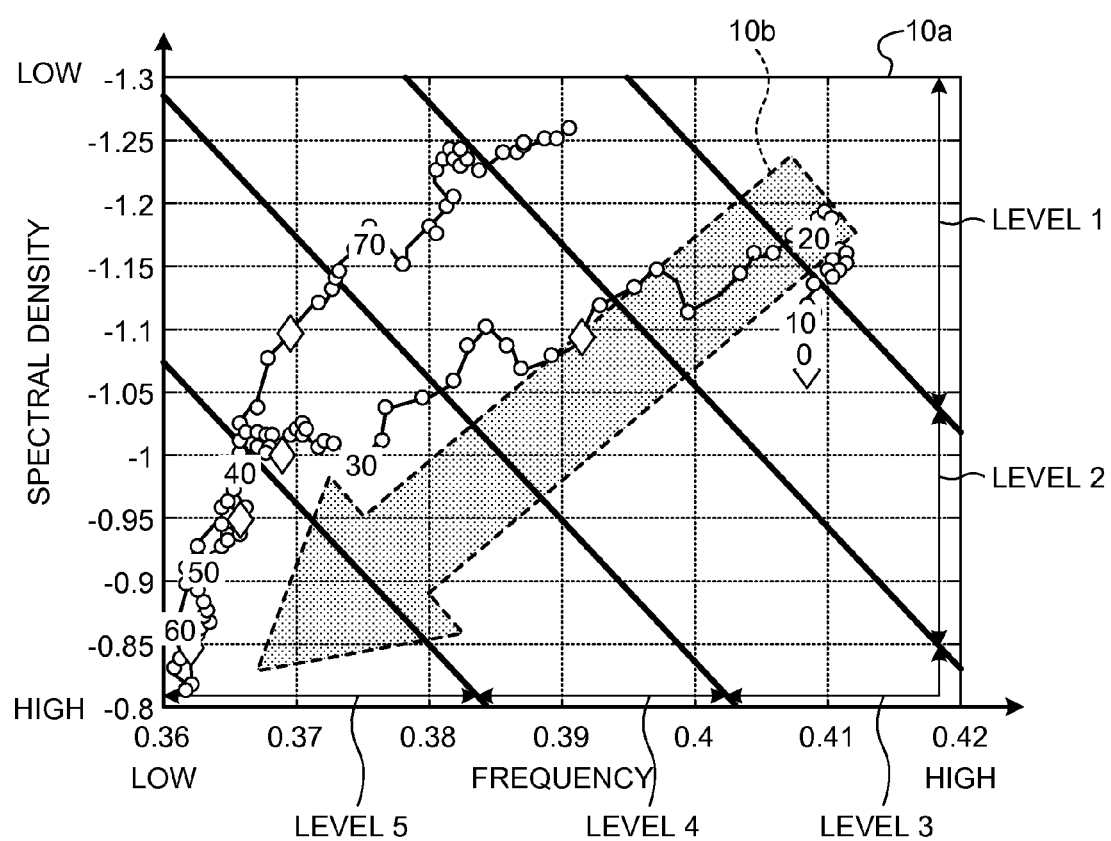
FIG. 15 is a diagram illustrating an example of a scale set by a setting unit.

Here, the scale set by the setting unit 160 is explained. FIG. 15 is a diagram illustrating an example of the scale set by the setting unit. The horizontal axis in FIG. 15 indicates frequency, and the vertical axis indicates spectral density. In the example illustrated in FIG. 15, a scale 10a is set so that the degree of sleepiness gets lower toward the upper right and gets higher toward the lower left as indicated by a sleepiness direction 10b. In this case, the scale 10a is divided into five areas from the upper right to the lower left, and the five areas are assigned five levels of sleepiness, respectively. That is, the degree of sleepiness increases with increasing sleepiness level determined by the scale 10a in order from level 1 to level 5; on the other hand, the level of arousal decreases with increasing the sleepiness level. The setting unit 160 holds therein the scale 10a normalized as illustrated in FIG. 15. Data in the scale set by the setting unit 160 is, for example, data which includes equations expressing boundaries between the areas in the scale and values of sleepiness level. Incidentally, in FIG. 15, there is described the case where the areas of the normalized scale 10a are equal in width; however, it is not limited to this. For example, respective widths of the areas of the normalized scale 10a can be adjusted to be narrower with increasing level of sleepiness. Furthermore, the data in the scale is not limited to the above-described organization, and can be composed of, for example, a frequency and spectral density at a reference point and a frequency and spectral density at an estimated point.

Figure 16:
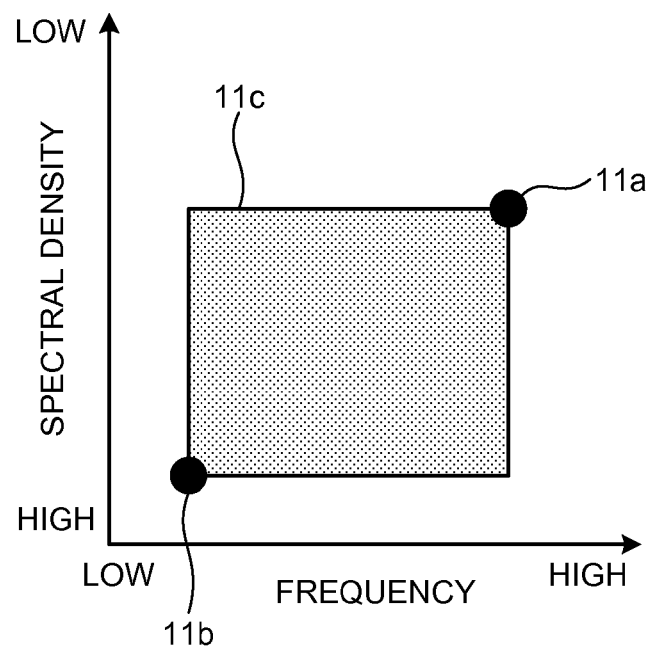
FIG. 16 is a diagram for explaining a scale setting process performed by the setting unit.

Subsequently, a scale setting process performed by the setting unit 160 is explained. FIG. 16 is a diagram for explaining the scale setting process performed by the setting unit. The horizontal axis in FIG. 16 indicates frequency, and the vertical axis indicates spectral density. As illustrated in FIG. 16, the setting unit 160 sets a normalized scale 11c by using a value of a reference point 11a and a value of an estimated point 11b. For example, the setting unit 160 makes a local maximum frequency value of the normalized scale 11c correspond to a frequency at the reference point 11a. The setting unit 160 makes a minimum spectral density value of the normalized scale 11c correspond to spectral density at the reference point 11a. The setting unit 160 makes a minimum frequency value of the normalized scale 11c correspond to a frequency at the estimated point 11b. The setting unit 160 makes a local maximum spectral density value of the normalized scale 11c correspond to spectral density at the estimated point 11b. The setting unit 160 divides the corresponding scale 11c into five equal parts, and sets areas corresponding to levels of sleepiness. The setting unit 160 calculates equations expressing boundaries between the set areas in the scale 11c, thereby setting subject's scale 11c. Then, the setting unit 160 stores the set scale in the storage unit 170.

Return to the explanation of FIG. 1. The storage unit 170 stores therein an index of arousal level set by the setting unit 160. For example, the storage unit 170 stores therein subject's scale set by the setting unit 160 in a manner associated with identification information which identifies the subject.

The determining unit 180 determines subject's arousal level by comparing a feature amount calculated by the calculating unit 130 and an index of arousal level set by the setting unit 160. For example, the determining unit 180 receives input of identification information by a subject, and reads out a scale corresponding to the identification information from the storage unit 170. Then, the determining unit 180 determines which area of the scale a local maximum point calculated by the calculating unit 130 is included. Specifically, for example, the determining unit 180 substitutes a local maximum frequency and local maximum spectral density at the local maximum point into respective equations expressing the areas in the scale, thereby determining an area in which the calculated local maximum point is included. Then, the determining unit 180 determines subject's sleepiness level according to the area determined to include the local maximum point. Incidentally, a method for receiving identification information is not limited to the above-described method. For example, the determining unit 180 can use a method to acquire identification information from a camera image of the current subject taken and a method to determine an individual using a region of a heartbeat signal characteristic of the individual, etc.

Furthermore, the determining unit 180 determines subject's state and the level of risk by using the feature amount calculated by the calculating unit 130 and the determined sleepiness level. For example, the determining unit 180 determines subject's state by comparing the local maximum frequency, local maximum spectral density, and width of a spectrum waveform calculated by the calculating unit 130 with those calculated in a previous time. The previous time to be compared can be the last or last but several calculations, or can be a given time ago, such as a few seconds to a few minutes ago. Furthermore, the previous time to be compared is not limited to these examples, and can be set to any value by a person who uses the arousal-level determining apparatus 100. For example, when the local maximum frequency is equal to or lower than the previous local maximum frequency, the local maximum spectral density is equal to or lower than the previous local maximum spectral density, and the width of the spectrum waveform has increased, the determining unit 180 determines that the subject is in a state of struggle against sleepiness. Furthermore, when the local maximum frequency is equal to or lower than the previous local maximum frequency, but the local maximum spectral density is not equal to or lower than the previous local maximum spectral density or the width of the spectrum waveform has not increased, the determining unit 180 determines that the subject is in a sleepy state. Moreover, when the local maximum frequency is not equal to or lower than the previous local maximum frequency, the local maximum spectral density is equal to or higher than the previous local maximum spectral density, and the width of the spectrum waveform has decreased, the determining unit 180 determines that the subject is in a state of concentration. Furthermore, when the local maximum frequency is not equal to or lower than the previous local maximum frequency, but the local maximum spectral density has not increased from the previous local maximum spectral density or the width of the spectrum waveform has not decreased, the determining unit 180 determines that the subject is in an arousal state.

As a result of the determination, if the subject is in a state of struggle against sleepiness, the determining unit 180 determines a change in sleepiness level, and, when the sleepiness level has increased, the determining unit 180 determines that the subject does not achieve an arousal effect even by the struggle against sleepiness, and determines that the level of risk is 5 denoting the highest risk. Furthermore, when the subject is in a state of struggle against sleepiness, and the sleepiness level has decreased, the determining unit 180 determines that the subject has achieved an arousal effect even by the struggle against sleepiness, and determines that the level of risk is 1, then, when the sleepiness level is unchanged, determines that the subject maintains the struggle against sleepiness, and determines that the level of risk is 2. Moreover, when the subject is in a sleepy state, the determining unit 180 finds an amount of transition in a direction toward higher sleepiness level since a given time ago on the basis of changes in local maximum frequency and local maximum spectral density. This given time is, for example, 10 seconds. This given time is not limited to this example, and can be set to any value by a person who uses the arousal-level determining apparatus 100. The determining unit 180 determines whether the transition amount is equal to or more than a given amount, and, if the transition amount is equal to or more than the given amount, determines that the change to a sleepiness direction comes fast, and determines that the level of risk is 4; on the other hand, if the transition amount is less than the given amount, the determining unit 180 determines that the level of risk is 3. Then, the determining unit 180 outputs a result of the determination to the output unit 220.

The receiving unit 190 receives an instruction to correct a feature amount calculated by the calculating unit 130 from a subject. For example, the receiving unit 190 corresponds to a touch panel. For example, when the estimating unit 150 has set a reference point, the receiving unit 190 inquires of the subject about the current sleepiness level. Then, for example, when the current sleepiness level received from the subject is not "1", the receiving unit 190 outputs the received subject's current sleepiness level to the correcting unit 200. On the other hand, when the current sleepiness level received from the subject is "1" or when the receiving unit 190 has not received the current sleepiness level from the subject within a given time, the receiving unit 190 ends the process, and waits until the estimating unit 150 sets a reference point again.

The correcting unit 200 corrects a feature amount to be a reference index of arousal level on the basis of an instruction received by the receiving unit 190. For example, the correcting unit 200 adds given values to the local maximum frequency and local maximum spectral density at the reference point set by the estimating unit 150 according to subject's current sleepiness level received from the receiving unit 190, respectively, thereby moving the reference point. Then, the correcting unit 200 sets the moved reference point as a corrected reference point. Here, the given value added to the local maximum frequency is, for example, "0.02"; the given value added to the local maximum spectral density is, for example, "−0.2". The given values are not limited to these examples, and can be set to any values according to subject's current sleepiness level by a person who uses the arousal-level determining apparatus 100.

Figure 17:
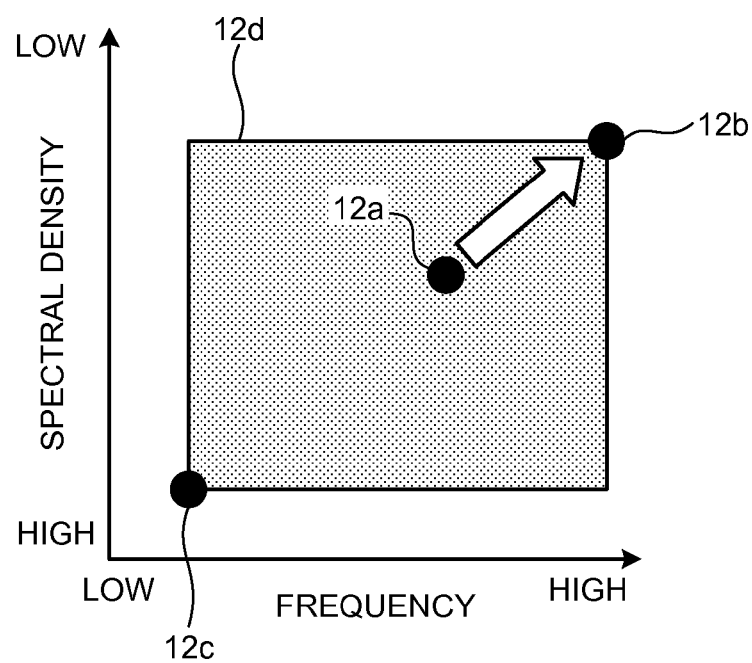
FIG. 17 is a diagram for explaining a reference-point correcting process performed by a correcting unit.

FIG. 17 is a diagram for explaining a reference-point correcting process performed by the correcting unit. The horizontal axis in FIG. 17 indicates frequency, and the vertical axis indicates spectral density. As illustrated in FIG. 17, for example, when subject's current sleepiness level is "2", the correcting unit 200 adds "0.02" to a local maximum frequency at a reference point 12*a*, and adds "−0.2" to local maximum spectral density at the reference point 12*a*, thereby moving the reference point 12*a* to a reference point 12*b*. Then, the correcting unit 200 sets the reference point 12*b* as a corrected reference point. Incidentally, an estimated point estimated on the basis of the reference point 12*b* is an estimated point 12*c*. Furthermore, a scale set on the basis of the reference point 12*b* and the estimated point 12*c* is a scale 12*d*.

Incidentally, why the correcting unit 200 corrects a reference point is because although a reference point is set by using a feature amount at a time when subject's sleepiness level is considered to be "1", subject's sleepiness level at this time is not always "1". For example, if a subject starts driving in a state where the subject experiences sleepiness, the estimating unit 150 incorrectly sets the local maximum frequency and local maximum spectral density calculated at a time when sleepiness level is not "1" as a reference point, and further estimates an estimated point by using the incorrect reference point. Therefore, to estimate an estimated correctly, the correcting unit 200 corrects the incorrectly-set reference point by receiving subject's current sleepiness level from the receiving unit 190.

The expanding unit 210 expands an index of arousal level if a feature amount calculated by the calculating unit 130 is out of a preset range of the index of arousal level. For example, when the expanding unit 210 has acquired the local maximum frequency and local maximum spectral density calculated by the calculating unit 130 from the estimating unit 150, the expanding unit 210 determines whether or not the acquired value is off subject's scale stored in the storage unit 170.

When the acquired value is off the scale, the expanding unit 210 determines whether or not the distance between the acquired value and the scale is equal to or more than a threshold. When the distance is not equal to or more than the threshold, the expanding unit 210 expands subject's scale, and stores the expanded scale in the storage unit 170. On the other hand, when the distance is equal to or more than the threshold, the expanding unit 210 waits until a local maximum frequency and local maximum spectral density have been acquired again. Incidentally, the threshold used here is a value for eliminating an error in analysis of heartbeat signals; for example, a threshold for a value of local maximum frequency is 0.1. This is, when a value of local maximum frequency deviates 0.1 or more from the scale, to determine that a different local maximum point has been detected. The threshold is not limited to this example, and can be set to any value by a person who uses the arousal-level determining apparatus 100.

Figure 18:
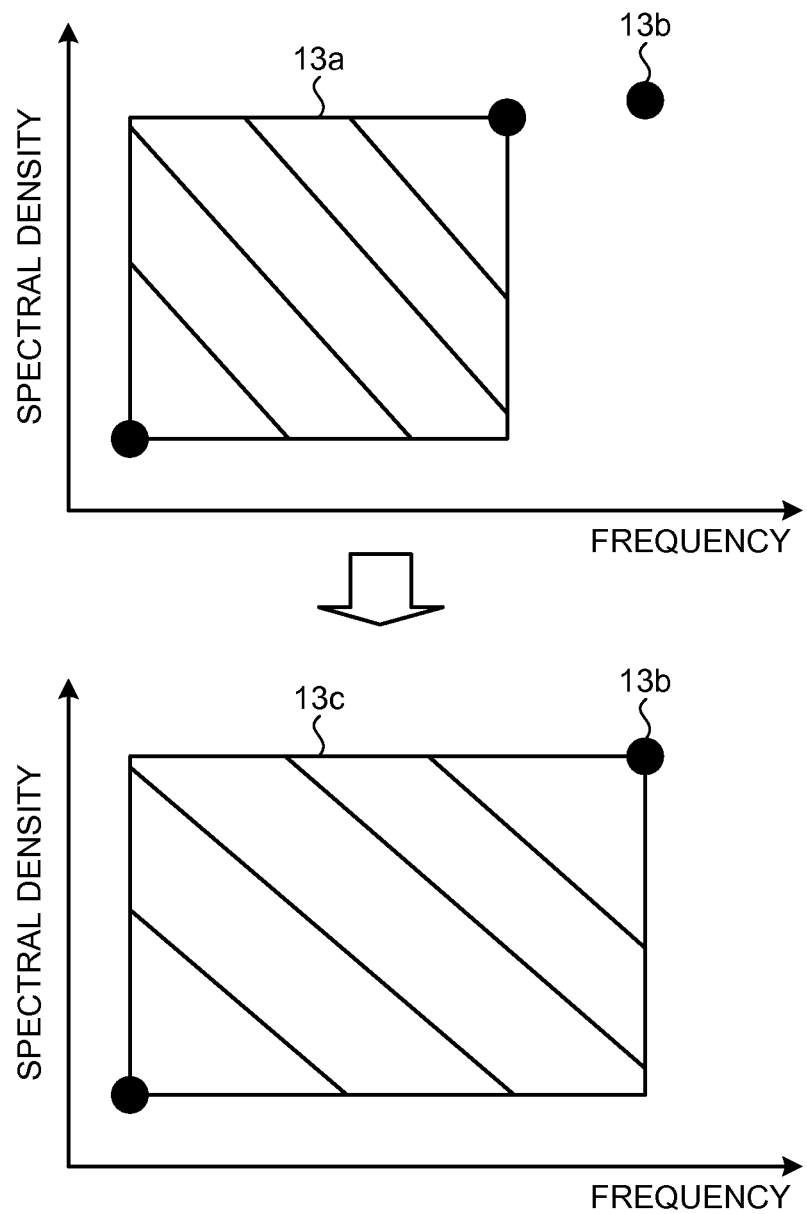
FIG. 18 is a diagram for explaining an overall scale expanding process performed by an expanding unit.

A scale expanding process performed by the expanding unit 210 is explained. For example, the expanding unit 210 moves sides of a preset scale so that the scale includes an off-scale value. Then, the expanding unit 210 sets a scale by applying a normalized scale to sides, thereby expanding the scale overall. FIG. 18 is a diagram for explaining the overall scale expanding process performed by the expanding unit. The horizontal axis in FIG. 18 indicates frequency, and the vertical axis indicates spectral density. As illustrated in FIG. 18, the expanding unit 210 moves an upper side and right side of a preset scale 13*a* so that the scale 13*a* includes an off-scale value 13*b*. Then, the expanding unit 210 sets a scale 13*c* by applying a normalized scale to sides, thereby expanding the scale 13*a* overall.

Figure 19:
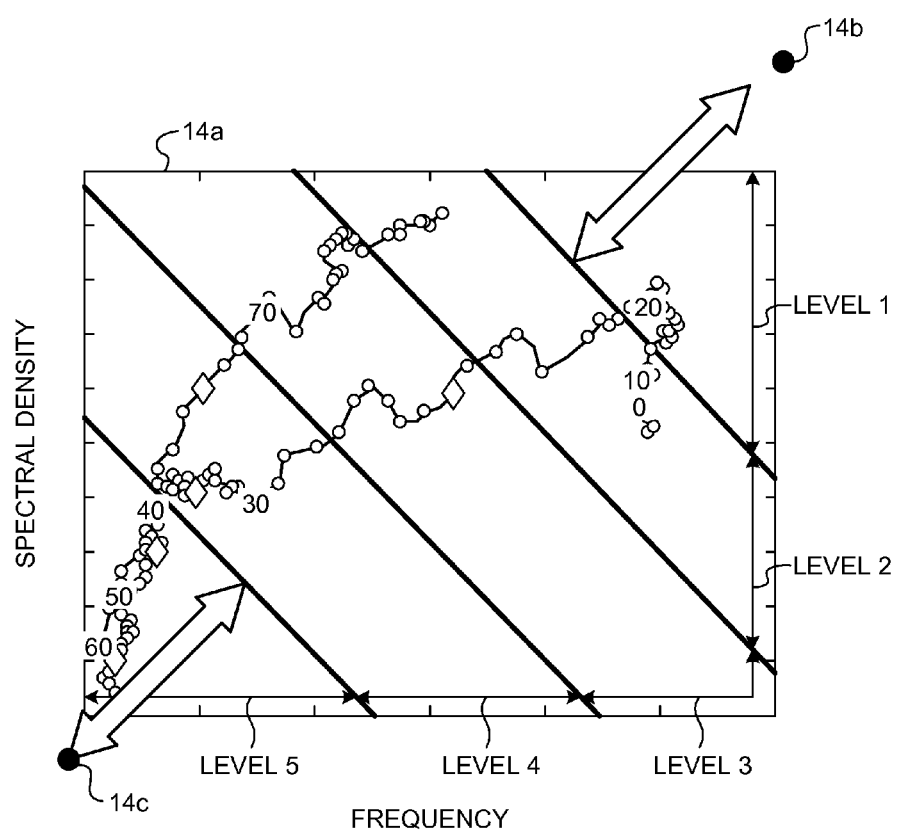
FIG. 19 is a diagram for explaining a partial scale expanding process performed by the expanding unit.

Furthermore, for example, the expanding unit 210 partially expands only an area in the preset scale closer to an off-scale value. FIG. 19 is a diagram for explaining a partial scale expanding process performed by the expanding unit. The horizontal axis in FIG. 19 indicates frequency, and the vertical axis indicates spectral density. As illustrated in FIG. 19, for example, when an off-scale value 14*b* exists in a direction of the upper right of a scale 14*a*, the expanding unit 210 expands only an area of level 1 with respect to the off-scale value 14*b*. Furthermore, for example, when an off-scale value 14*c* exists in a direction of the lower left of the scale 14*a*, the expanding unit 210 expands only an area of level 5 with respect to the off-scale value 14*c*.

Incidentally, why the expanding unit 210 expands the scale is because when the local maximum frequency and local maximum spectral density calculated by the calculating unit 130 is off the scale, it is difficult for the determining unit 180 to determine the sleepiness level. Therefore, the expanding unit 210 expands the scale so as to determine the sleepiness level even when the calculated local maximum frequency and local maximum spectral density is off the scale.

The output unit 220 outputs a result of determination by the determining unit 180. The output unit 220 corresponds to, for example, a monitor and a speaker, etc. Incidentally, the output unit 220 can be configured to output to a system of a vehicle. The output unit 220 performs various outputs according to subject's arousal level, subject's state, and risk level. For example, when subject's arousal level has decreased, when a subject is in a state of struggle against sleepiness or when the risk level is 3, the output unit 220 informs the subject or a person around the subject of the risk though the monitor. Furthermore, when a subject is in a sleepy state in which the subject has a higher risk or when the risk level is 4 or higher, the output unit 220 produces a warning sound through the speaker to inform the subject of the risk. Moreover, when the risk level is 5 which is the highest risk level, the output unit 220 outputs a signal urging to halt a vehicle to a system of the vehicle, thereby causing the system of the vehicle to halt the vehicle.

[Flow of Processing]

Figure 20:
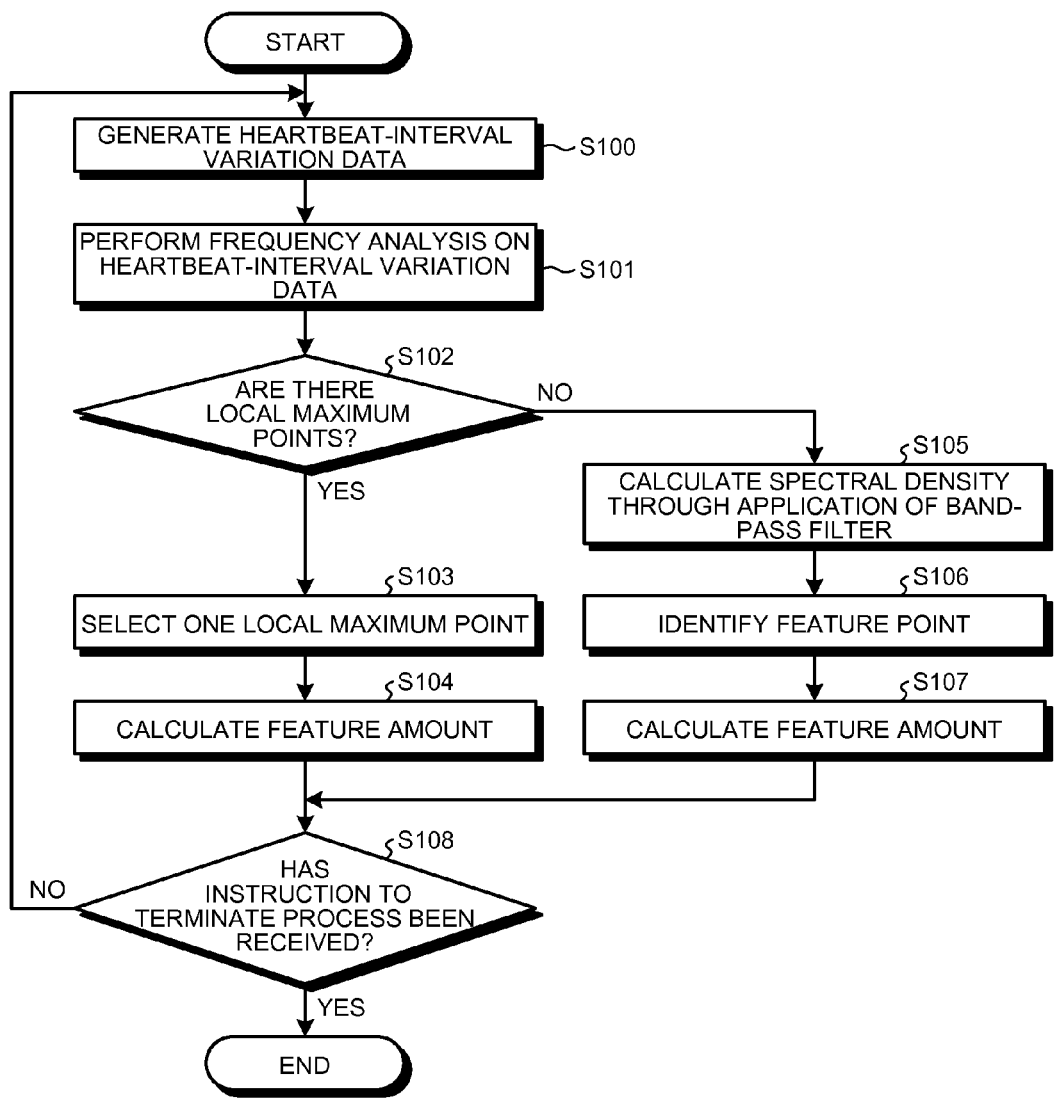
FIG. 20 is a flowchart illustrating a procedure of an identifying process.

Subsequently, the flow of a feature-point identifying process performed by the arousal-level determining apparatus 100 according to the present embodiment is explained. FIG. 20 is a flowchart illustrating a procedure of the identifying process. This identifying process is performed, for example, upon start-up of a system of a vehicle equipped with the arousal-level determining apparatus 100.

As illustrated in FIG. 20, the generating unit 120 detects heartbeat signal data detected by the detecting unit for a given length of time, and generates heartbeat-interval variation data which indicates changes in heartbeat interval (Step S100). The calculating unit 130 performs frequency analysis on the heartbeat-interval variation data, and calculates spectral density with respect to each frequency (Step S101).

The calculating unit 130 determines whether there exist local maximum points in a HF component of the calculated spectral density (Step S102). When local maximum points exist (YES at Step S102), the calculating unit 130 selects one local maximum point included in the HF component from among the local maximum points at which spectral density is maximum (Step S103). That is, each time the calculating unit 130 calculates spectral density, the calculating unit 130 generates spectral density data which indicates spectral density at each frequency, and selects one local maximum point included in the HF component from among local maximum points at which spectral density of the spectral density data is maximum. The calculating unit 130 calculates a feature amount at the selected local maximum point (Step S104). That is, the calculating unit 130 calculates a local maximum frequency and local maximum spectral density at the selected local maximum point. Furthermore, the calculating unit 130 calculates the width of a spectrum waveform at a certain height L from the selected local maximum point.

On the other hand, when no local maximum point exists (NO at Step S102), the calculating unit 130 calculates spectral density with respect to each frequency band in the heartbeat-interval variation data by applying a band-pass filter to the frequency band while changing the frequency band (Step S105). The identifying unit 140 identifies a feature point corresponding to a spectral density peak in respective spectral densities in the frequency bands calculated by the calculating unit 130 (Step S106). The calculating unit 130 calculates a feature amount at the feature point corresponding to a spectral density peak (Step S107). That is, the calculating unit 130 calculates a local maximum frequency and local maximum spectral density at the feature point corresponding to a spectral density peak. Furthermore, the calculating unit 130 calculates the width of a spectrum waveform at a certain height L from the feature point corresponding to a spectral density peak.

The calculating unit 130 determines whether an instruction to terminate the process has been received or not (Step S108). For example, when an instruction to terminate the process has been received from a system of the vehicle (YES at Step S108), the process is terminated. On the other hand, when an instruction to terminate the process has not been received (NO at Step S108), the process moves on to the above-described Step S100.

Figure 21:
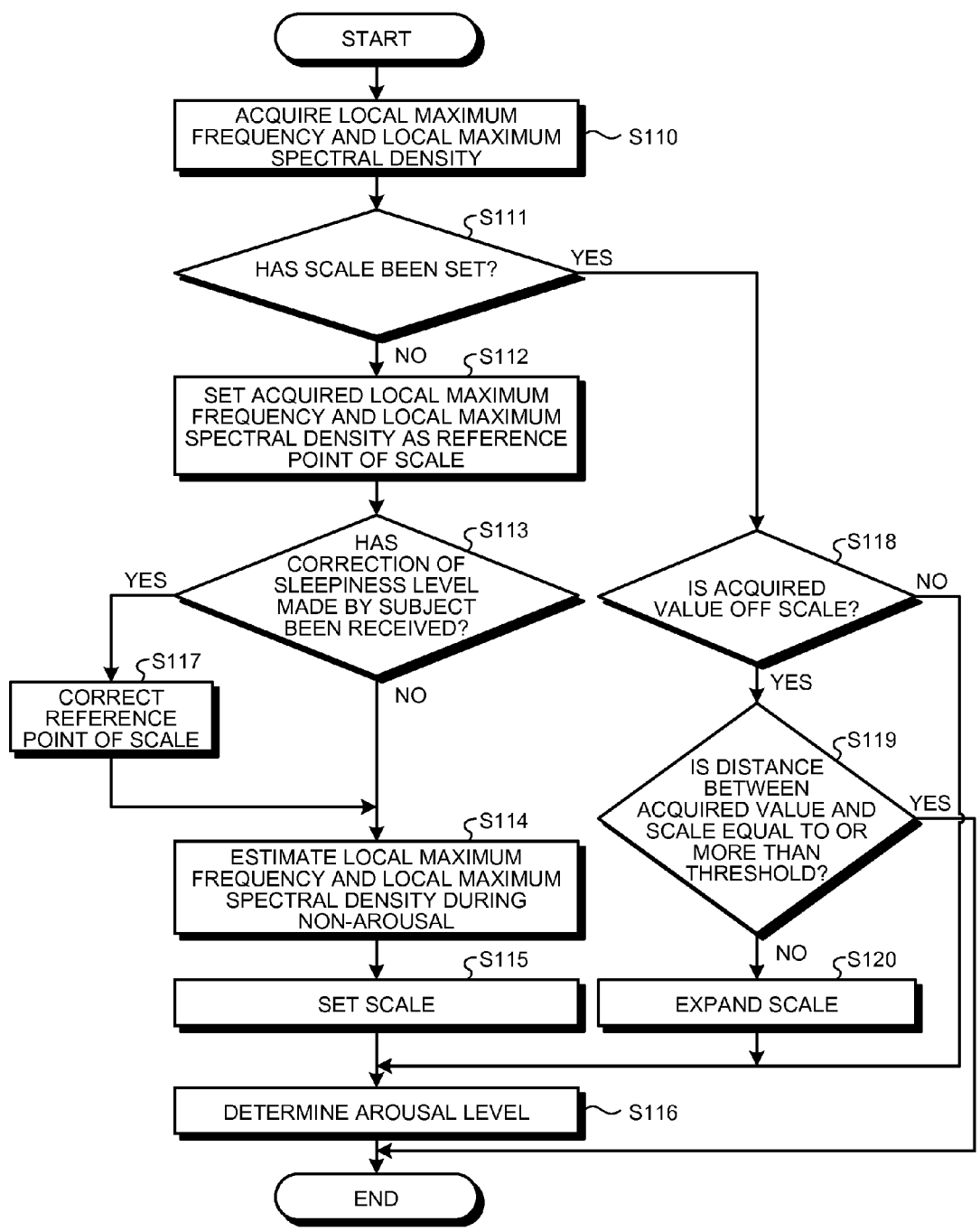
FIG. 21 is a flowchart illustrating a procedure of a sleepiness-level determining process.

Subsequently, the flow of a sleepiness-level determining process performed by the arousal-level determining apparatus 100 according to the present embodiment is explained. FIG. 21 is a flowchart illustrating a procedure of the sleepiness-level determining process. This sleepiness-level determining process is performed, for example, each time a feature amount is calculated by the calculating unit 130.

As illustrated in FIG. 21, the estimating unit 150 acquires a local maximum frequency and local maximum spectral density calculated by the calculating unit 130 from the calculating unit 130 (Step S110). The estimating unit 150 determines whether subject's scale has been set or not (Step S111). When subject's scale has not been set (NO at Step S11), the estimating unit 150 sets the acquired local maximum frequency and local maximum spectral density as a reference point of a scale (Step S112).

The estimating unit 150 determines whether correction of sleepiness level made by the subject has been received or not (Step S113). When correction of sleepiness level made by the subject has not been received (NO at Step S113), the estimating unit 150 estimates a local maximum frequency and local maximum spectral density during non-arousal (Step S114). That is, when the current sleepiness level that the receiving unit 190 has received from the subject is "1" or when the current sleepiness level has not received from the subject within a given time, the estimating unit 150 substitutes a value of the set reference point into a linear regression equation, thereby calculating a value during non-arousal, and sets the calculated value as an estimated point. Then, the estimating unit 150 outputs the reference point and the estimated point to the setting unit 160.

The setting unit 160 sets a scale on the basis of the reference point and estimated point received from the estimating unit 150 (Step S115). That is, the setting unit 160 calculates respective change amounts of frequency and spectral density, which change between during arousal and during non-arousal, from respective local maximum frequencies and local maximum spectral densities at the reference point 11a and the estimated point 11b received from the estimating unit 150. The setting unit 160 makes the normalized scale 10a correspond to the calculated change amounts of frequency and spectral density, thereby setting subject's scale. Then, the setting unit 160 stores the set scale in the storage unit 170.

The determining unit 180 determines subject's arousal level by comparing the local maximum frequency and local maximum spectral density calculated by the calculating unit 130 and the scale (Step S116). That is, the determining unit 180 determines subject's sleepiness level according to an area of the scale in which the local maximum frequency and local maximum spectral density calculated by the calculating unit 130 are included.

On the other hand, when correction of sleepiness level made by the subject has been received (YES at Step S113), the estimating unit 150 corrects the reference point of the scale (Step S117), and moves on to Step S114. That is, the correcting unit 200 adds given values to the local maximum frequency and local maximum spectral density at the reference point set by the estimating unit 150 according to subject's current sleepiness level received from the receiving unit 190, respectively, thereby moving the reference point. Then, the correcting unit 200 sets the moved reference point as a corrected reference point.

On the other hand, when subject's scale has been set (YES at Step S111), the estimating unit 150 outputs the acquired local maximum frequency and local maximum spectral density to the expanding unit 210.

When the expanding unit 210 has acquired the local maximum frequency and local maximum spectral density calculated by the calculating unit 130 from the estimating unit 150, the expanding unit 210 determines whether or not the acquired value is off subject's scale stored in the storage unit 170 (Step S118). When the acquired value is off the scale (YES at Step S118), the expanding unit 210 determines whether or not the distance between the acquired value and the scale is equal to or more than a threshold (Step S119). When the distance is not equal to or more than the threshold (NO at Step S119), the expanding unit 210 expands subject's scale (Step S120), and moves on to Step S116.

On the other hand, when the distance is equal to or more than the threshold (YES at Step S119), the expanding unit 210 terminates the process, and waits until a local maximum frequency and local maximum spectral density have been acquired again.

On the other hand, when the acquired value is not off the scale (NO at Step S118), the expanding unit 210 moves on to Step S116.

Incidentally, in the above-described processing procedure, the processes for correcting the reference point at Steps S113 and S117 do not necessarily have to be performed. That is, after the process at Step S112 has been performed, the process at Step S114 can be performed.

Furthermore, in the above-described processing procedure, the processes for expanding the scale at Steps S118 to S120 do not necessarily have to be performed. That is, at Step S111, when it has been determined that subject's scale has been set, the process at Step S116 can be performed.

Figure 22A:
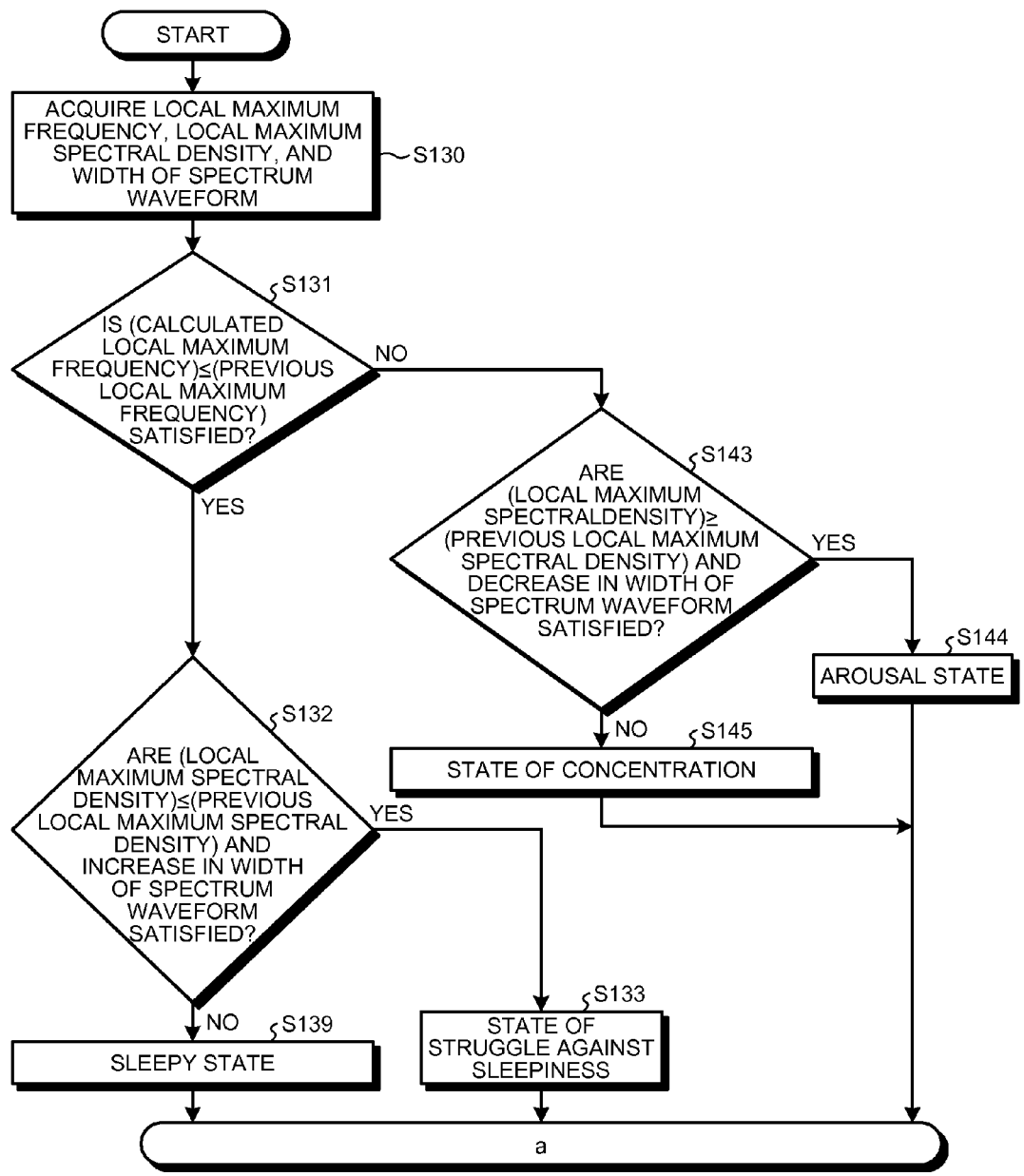
FIG. 22A is a flowchart illustrating a procedure of a risk-level determining process.
Figure 22B:
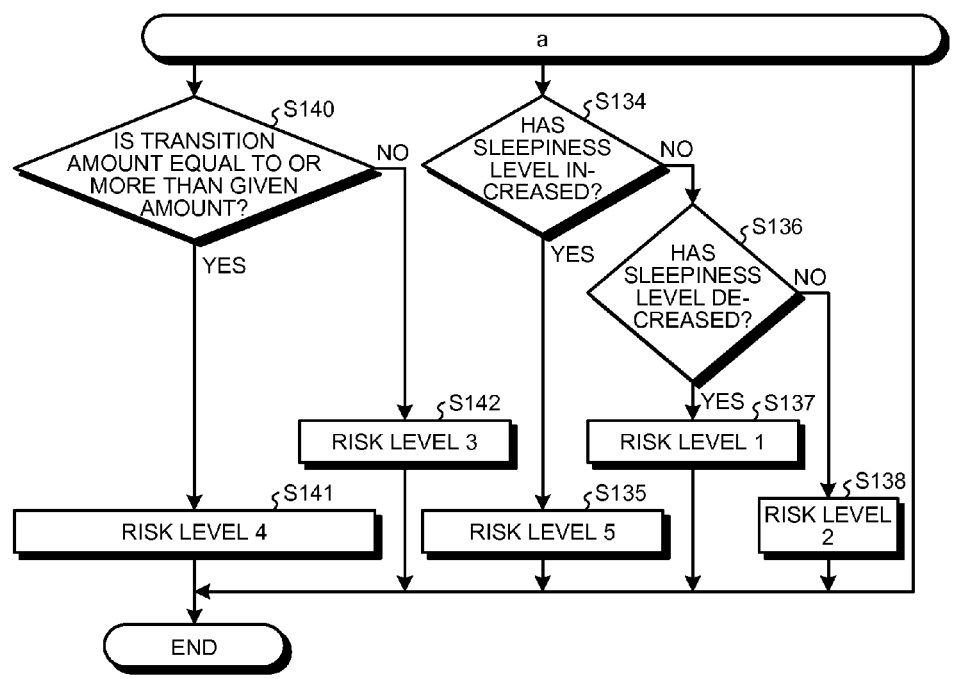
FIG. 22B is a flowchart illustrating a procedure of a risk-level determining process.

Subsequently, the flow of a risk-level determining process performed by the arousal-level determining apparatus 100 according to the present embodiment is explained. FIG. 22A and FIG. 22B is a flowchart illustrating a procedure of the risk-level determining process. This risk-level determining process is performed, for example, each time a feature amount is calculated by the calculating unit 130.

As illustrated in FIG. 22A and FIG. 22B, the determining unit 180 acquires the calculated local maximum frequency, local maximum spectral density, and width of the spectrum waveform from the calculating unit 130 (Step S130). The determining unit 180 determines whether or not the local maximum frequency calculated by the calculating unit 130 is equal to or lower than a local maximum frequency calculated in a previous time (Step S131). When the local maximum frequency is equal to or lower than a local maximum frequency calculated in a previous time (YES at Step S131), the determining unit 180 determines whether or not the local maximum spectral density is equal to or lower than a previous local maximum spectral density and the width of the spectrum waveform has increased (Step S132). When the local maximum spectral density is equal to or lower than a local maximum spectral density calculated in the previous time and the width of the spectrum waveform has increased (YES at Step S132), the determining unit 180 determines that a subject is in a state of struggle against sleepiness (Step S133). Then, the determining unit 180 determines whether the sleepiness level has increased (Step S134). When the sleepiness level has increased (YES at Step S134), the determining unit 180 determines that the risk level is (Step S135), and terminates the process. On the other hand, when the sleepiness level has not increased (NO at Step S134), the determining unit 180 determines whether the sleepiness level has decreased (Step S136). When the sleepiness level has decreased (YES at Step S136), the determining unit 180 determines that the risk level is 1 (Step S137), and terminates the process. On the other hand, when the sleepiness level has not decreased (NO at Step S136), the determining unit 180 determines that the risk level is 2 (Step S138), and terminates the process.

On the other hand, when the local maximum spectral density is not equal to or lower than a local maximum spectral density calculated in the previous time or the width of the spectrum waveform has not increased (NO at Step S132), the determining unit 180 determines that the subject is in a sleepy state (Step S139). Then, the determining unit 180 finds an amount of transition in a direction toward higher sleepiness level, and determines whether the transition amount is equal to or more than a given amount (Step S140). When the transition amount is equal to or more than a given amount (YES at Step S140), the determining unit 180 determines that the risk level is 4 (Step S141), and terminates the process. On the other hand, when the transition amount is not equal to or more than a given amount (NO at Step S140), the determining unit 180 determines that the risk level is 3 (Step S142), and terminates the process.

On the other hand, when the local maximum frequency is not equal to or lower than a local maximum frequency calculated in the previous time (NO at Step S131), the determining unit 180 determines whether or not the local maximum spectral density is equal to or more than local maximum spectral density calculated in the previous time and the width of the spectrum waveform has decreased (Step S143). When the local maximum spectral density is equal to or more than local maximum spectral density calculated in the previous time and the width of the spectrum waveform has decreased (YES at Step S143), the determining unit 180 determines that the subject is in a state of concentration (Step S144), and terminates the process. On the other hand, when the local maximum spectral density is not equal to or more than local maximum spectral density calculated in the previous time or the width of the spectrum waveform has not decreased (NO at Step S143), the determining unit 180 determines that the subject is in an arousal state (Step S145), and terminates the process.

Subsequently, the effect of the arousal-level determining apparatus 100 according to the present first embodiment is explained. The arousal-level determining apparatus 100 according to the present first embodiment generates heartbeat-interval variation data, which indicates changes in heartbeat interval, on the basis of heartbeat signals indicating subject's heartbeats. The arousal-level determining apparatus 100 applies a band-pass filter, which allows passage of a certain range of frequencies, to each frequency band in the heartbeat-interval variation data while changing the frequency band, and calculates spectral density with respect to each frequency band applied with the band-pass filter. The arousal-level determining apparatus 100 identifies a feature point corresponding to a spectral density peak in the calculated spectral densities in the frequency bands. The arousal-level determining apparatus 100 determines subject's arousal level on the basis of the identified feature point. Accordingly, the arousal-level determining apparatus 100 can determine subject's arousal level.

Furthermore, the arousal-level determining apparatus 100 according to the present first embodiment calculates spectral density with respect to each frequency band while changing the frequency band applied with the band-pass filter to be partially overlapped with a previous frequency band applied. Here, when spectral density is calculated through the application of the band-pass filter without overlap between frequency bands, if a spectral density peak is located in a zone between frequency bands applied with the band-pass filter, it is hard to determine the peak position of spectral density. On the other hand, the arousal-level determining apparatus 100 calculates spectral density with respect to each frequency band while changing the frequency band applied with the band-pass filter to be partially overlapped with a previous frequency band applied, and therefore can determine the peak position of spectral density accurately.

Moreover, the arousal-level determining apparatus 100 according to the present first embodiment calculates spectral density through the application of a band-pass filter that allows passage of a range of frequencies in which the feature point shifts with a change in arousal level. Accordingly, the arousal-level determining apparatus 100 can extract heartbeat-interval variation data for a range of frequencies in which change is produced by a change in arousal level, and therefore can detect a shift in the feature point accurately.

Furthermore, the arousal-level determining apparatus 100 according to the present first embodiment calculates spectral density by applying the band-pass filter to each frequency band while changing the frequency band within a frequency range of a HF component. Accordingly, the arousal-level determining apparatus 100 can accurately determine a change in arousal level from a parasympathetic nervous state.

Moreover, the arousal-level determining apparatus 100 according to the present first embodiment calculates spectral density from heartbeat-interval variation data, and, if no local maximum point exists in the calculated spectral density, calculates spectral density through the application of the band-pass filter. Accordingly, when a local maximum point exists in the spectral density calculated from the heartbeat-interval variation data, the arousal-level determining apparatus 100 can omit a process of identifying a feature point through the application of the band-pass filter. Furthermore, when no local maximum point exists in the spectral density calculated from the heartbeat-interval variation data, the arousal-level determining apparatus 100 identifies a feature point through the application of the band-pass filter, thereby can determine subject's arousal level.

Incidentally, the above-described processing units, i.e., the detecting unit 110, the generating unit 120, the calculating unit 130, the identifying unit 140, the estimating unit 150, the setting unit 160, the determining unit 180, the receiving unit 190, the correcting unit 200, and the expanding unit 210 correspond to, for example, the following devices. That is, these processing units correspond to integrated devices such as an application specific integrated circuit (ASIC) and a field programmable gate array (FPGA). Furthermore, these processing units correspond to electronic circuits such as a central processing unit (CPU) and a micro processing unit (MPU).

Furthermore, the storage unit 170 corresponds to, for example, semiconductor memory devices, such as a random access memory (RAM), a read only memory (ROM), and a flash memory, and storage devices, such as a hard disk and an optical disk.

Incidentally, the configuration of the arousal-level determining apparatus 100 illustrated in FIG. 1 is just an example, and the arousal-level determining apparatus 100 does not necessarily have to include all the processing units illustrated in FIG. 1. For example, the arousal-level determining apparatus 100 only has to include a generating unit, a calculating unit, an identifying unit, and a determining unit.

That is, the generating unit generates heartbeat-interval variation data, which indicates changes in heartbeat interval, on the basis of heartbeat signals indicating subject's heartbeats. The calculating unit applies a band-pass filter, which allows passage of a certain range of frequencies, to each frequency band in the heartbeat-interval variation data while changing the frequency band, and calculates spectral density with respect to each frequency band applied with the band-pass filter. The identifying unit identifies a feature point corresponding to a spectral density peak in the calculated spectral densities in the frequency bands. The determining unit determines subject's arousal level on the basis of the identified feature point, thereby can determine subject's arousal level.

Second Embodiment

Another embodiment of the arousal-level determining apparatus, arousal-level determining program, and arousal-level determining method discussed in the present application is explained below.

In the above first embodiment, there is described the case where the arousal-level determining apparatus 100 determines subject's sleepiness level by using a local maximum frequency and local maximum spectral density; however, the present invention is not limited to this. That is, the arousal-level determining apparatus 100 can be configured to determine subject's sleepiness by using either one of a local maximum frequency and local maximum spectral density. For example, the arousal-level determining apparatus 100 generates spectral density data on the basis of subject's heartbeat signals, and acquires a local maximum point from a HF component of the generated spectral density data. Using the fact that the local maximum point is correlated between during arousal and during non-arousal, the arousal-level determining apparatus 100 estimates a local maximum frequency during non-arousal from the acquired local maximum frequency. The arousal-level determining apparatus 100 divides a range in which a local maximum frequency changes between during arousal and during non-arousal into, for example, five equal parts, thereby setting an index of arousal level. The arousal-level determining apparatus 100 determines subject's arousal level by comparing a local maximum frequency calculated from subject's heartbeat signals with the index of arousal level.

Out of the processes explained in the first embodiment, all or part of the process described as an automatically-performed process can be manually performed, or all or part of the process described as a manually-performed process can be automatically performed by a publicly-known method. For example, a series of processing by the arousal-level determining apparatus 100 illustrated in FIG. 20 can be performed upon receipt of a driver's instruction after start-up of a system of a vehicle equipped with the arousal-level determining apparatus 100.

Furthermore, the processing procedures, control procedures, specific names, and information including various data and parameters illustrated in the above description and the drawings can be arbitrarily changed unless otherwise specified. For example, data of a scale set by the setting unit 160 can be composed of a frequency and spectral density at a reference point and a frequency and spectral density at an estimated point. In this case, values of the reference point and estimated point are stored in the storage unit 170, so the determining unit 180 applies a normalized scale to the values of the reference point and estimated point read out from the storage unit 170 and resets a scale, and then determines subject's sleepiness level.

Moreover, components of the arousal-level determining apparatus 100 illustrated in FIG. 1 are functionally conceptual ones, and do not necessarily have to be physically configured as illustrated in the drawing. That is, the specific forms of division and integration of components of the arousal-level determining apparatus 100 are not limited to those illustrated in the drawing, and all or some of the components can be configured to be functionally or physically divided or integrated in arbitrary units depending on various loads and usages, etc. For example, subject's arousal level can be determined in such a manner a server is configured to have any or all functions of units from the generating unit 120 to the expanding unit 210 illustrated in FIG. 1, and the server and the arousal-level determining apparatus 100 work together via a network.

Furthermore, the arousal-level determining apparatus 100 can be realized by equipping a known information processing apparatus with the functions of the arousal-level determining apparatus 100. The known information processing apparatus corresponds to devices, such as a personal computer, a workstation, a cell-phone, a personal handy-phone system (PHS) terminal, a mobile communication terminal, and a personal digital assistant (PDA).

Figure 23:
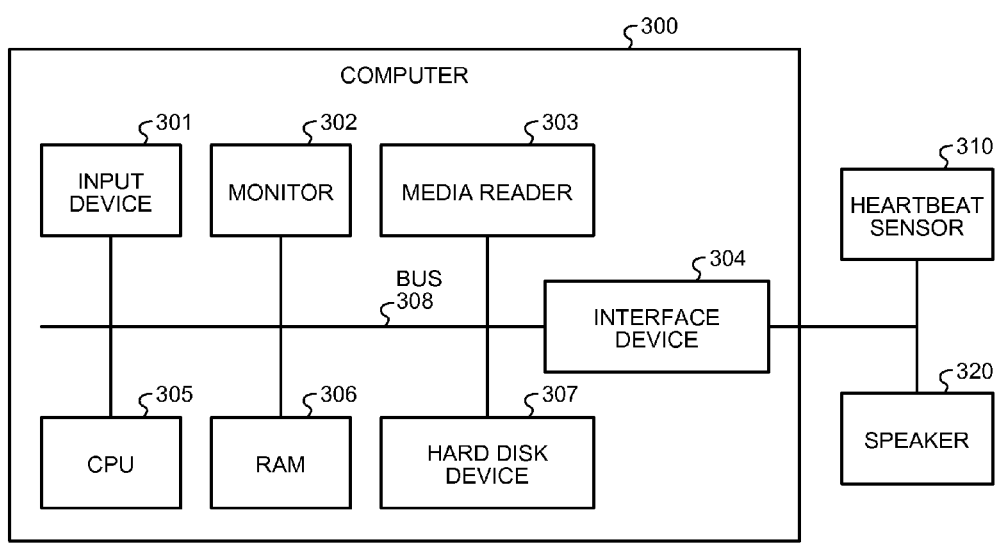
FIG. 23 is a diagram illustrating a computer that executes an arousal-level determining program.

FIG. 23 is a diagram illustrating a computer that executes the arousal-level determining program. As illustrated in FIG. 23, a computer 300 includes an input device 301 that receives data input from a user, a monitor 302, a media reader 303 that reads a program, etc. from a storage medium, and an interface device 304 that exchanges data with another device. Furthermore, the computer 300 includes a central processing unit (CPU) 305 that performs arithmetic processing, a random access memory (RAM) 306 that temporarily stores therein information, and a hard disk device 307. The devices 301 to 307 are connected by a bus 308. Furthermore, the computer 300 is connected to a heartbeat sensor 310, which detects subject's heartbeat signals, and a speaker 320 through the interface device 304.

The hard disk device 307 stores therein programs having the same functions as the generating unit 120, the calculating unit 130, the identifying unit 140, the estimating unit 150, the setting unit 160, the determining unit 180, the receiving unit 190, the correcting unit 200, and the expanding unit 210 illustrated in FIG. 1. Furthermore, the hard disk device 307 stores therein subject's scale in a manner associated with identification information which identifies the subject.

The CPU 305 reads out the programs from the hard disk device 307 and expands the programs into the RAM 306, thereby the programs work as processes. That is, the programs work as processes for performing the same processing as the generating unit 120, the calculating unit 130, the estimating unit 150, the setting unit 160, the determining unit 180, the receiving unit 190, the correcting unit 200, and the expanding unit 210.

Incidentally, the above-described programs do not necessarily have to be stored in the hard disk device 307. For example, the computer 300 can read and execute the programs stored in a computer-readable recording medium. The computer-readable recording medium corresponds to, for example, a portable recording medium such as a CD-ROM, a DVD, and a USB flash drive, a semiconductor memory such as a flash memory, and a hard disk drive, etc. Furthermore, the programs can be stored on a device connected to a public line, the Internet, a local area network (LAN), or a wide area network (WAN), etc., and the computer 300 can read the programs from the device and execute the programs.

REFERENCE SIGNS LIST

100 Arousal-level determining apparatus
110 Detecting unit
120 Generating unit
130 Calculating unit
140 Identifying unit
150 Estimating unit
160 Setting unit
170 Storage unit
180 Determining unit
190 Receiving unit
200 Correcting unit
210 Expanding unit
220 Output unit

The invention claimed is:

1. An arousal-level determining apparatus comprising:
a memory; and
a processor coupled to the memory executes a process configured to:
receive heartbeat signals for a subject;
generate heartbeat-interval variation data, which indicates changes in heartbeat intervals, on a basis of the heartbeat signals indicating the subject's heartbeats;
apply a plurality of times a band-pass filter, which allows passage of a frequency band of a certain range of frequencies, to the heartbeat-interval variation data, the frequency band being changed for each of the plurality of times, and calculate spectral densities with respect to each frequency band, by overlapping a range of frequencies within a first frequency band of the band-pass filter with a second frequency band of the band-pass filter that is nearest to the first frequency band, to detect peaks respectively of the calculated spectral densities;
identify as a feature point a peak in the calculated spectral densities based on the detected peaks; and
determine the arousal level of the subject on a basis of a spectral density and a frequency of the identified feature point, the arousal level inversely indicating a degree of sleepiness of the subject.

2. The arousal-level determining apparatus according to claim 1, wherein
the process is configured to apply the band-pass filter that allows passage of a range of frequencies in which the feature point shifts with respect to a change in arousal level of the subject.

3. The arousal-level determining apparatus according to claim 1, wherein
the process is configured to apply the band-pass filter to the heartbeat-interval variation data within a frequency range of a HF component.

4. The arousal-level determining apparatus according to claim 1, wherein
the process is configured to calculate spectral densities from the heartbeat-interval variation data, and, when no local maximum point exists in the calculated spectral densities, apply the band-pass filter to the heartbeat-interval variation data.

5. The arousal-level determining apparatus according to claim 1, wherein
the determining includes determining a change in the arousal level based on a change in a spectral density and a frequency of the identified feature point and in a width of a pulse made up of the detected peaks, and determining a risk level based on the determined arousal level and change therein; and
the process is further configured to output information or an operation to alert the subject to the determined risk level, the information or operation including a message displayed on a display unit or an alarm.

6. A non-transitory computer-readable recording medium having stored therein an arousal-level determining program causing a computer to execute a process comprising:
receiving heartbeat signals for a subject;
generating heartbeat-interval variation data, which indicates changes in heartbeat intervals, on a basis of the heartbeat signals indicating the subject's heartbeats;
applying a plurality of times a band-pass filter, which allows passage of a frequency band of a certain range of frequencies, to the heartbeat-interval variation data, the frequency band being changed for each of the plurality of times, and calculating spectral densities with respect to each frequency band, by overlapping a range of frequencies within a first frequency band of the band-pass filter with a second frequency band of the band-pass filter that is nearest to the first frequency band, to detect peaks respectively of the calculated spectral densities;
identifying as a feature point a peak in the calculated spectral densities based on the detected peaks; and
determining the arousal level of the subject on a basis of a spectral density and a frequency of the identified feature point, the arousal level inversely indicating a degree of sleepiness of the subject.

7. An arousal-level determining method by a computer, the arousal-level determining method comprising:
receiving heartbeat signals for a subject;
generating heartbeat-interval variation data, which indicates changes in heartbeat intervals, on a basis of the heartbeat signals indicating the subject's heartbeats;
applying a plurality of times a band-pass filter, which allows passage of a frequency band of a certain range of frequencies, to the heartbeat-interval variation data, the frequency band being changed for each of the plurality of times, and calculating spectral densities with respect to each frequency band, by overlapping a range of frequencies within a first frequency band of the band-pass filter with a second frequency band of the band-pass filter that is nearest to the first frequency band, to detect peaks respectively of the calculated spectral densities;
identifying as a feature point a peak in the calculated spectral densities based on the detected peaks; and
determining the arousal level of the subject on a basis of a spectral density and a frequency of the identified feature point, the arousal level inversely indicating a degree of sleepiness of the subject.

8. An arousal-level determining apparatus comprising:
a processor; and
a memory, wherein the processor executes a process comprising:
receiving heartbeat signals for a subject;
generating heartbeat-interval variation data, which indicates changes in heartbeat intervals, on a basis of the heartbeat signals indicating the subject's heartbeats;
storing the heartbeat-interval variation data in the memory;
applying a plurality of times a band-pass filter, which allows passage of a frequency band of a certain range of frequencies, to the heartbeat-interval variation data in the memory, the frequency band being changed for each of the plurality of times, and calculating spectral densities with respect to each frequency band, by overlapping a range of frequencies within a first frequency band of the band-pass filter with a second frequency band of the band-pass filter that is nearest to the first frequency band, to detect peaks respectively of the calculated spectral densities;
identifying as a feature point a peak in the calculated spectral densities based on the detected peaks; and
determining the arousal level of the subject on a basis of a spectral density and a frequency of the identified feature point, the arousal level inversely indicating a degree of sleepiness of the subject.

* * * * *